United States Patent
Co et al.

(10) Patent No.: US 11,521,722 B2
(45) Date of Patent: Dec. 6, 2022

(54) CAPTURING DETAILED STRUCTURE FROM PATIENT-DOCTOR CONVERSATIONS FOR USE IN CLINICAL DOCUMENTATION

(71) Applicant: Google LLC, Mountain View, CA (US)

(72) Inventors: Christopher Co, Saratoga, CA (US); Gang Li, Elkton, MD (US); Philip Chung, San Francisco, CA (US); Justin Paul, San Francisco, CA (US); Daniel Shing Shun Tse, San Francisco, CA (US); Katherine Chou, Palo Alto, CA (US); Diana Jaunzeikare, San Francisco, CA (US); Alvin Rajkomar, Mountain View, CA (US)

(73) Assignee: Google LLC, Mountain View, CA (US)

( * ) Notice: Subject to any disclaimer, the term of this patent is extended or adjusted under 35 U.S.C. 154(b) by 0 days.

(21) Appl. No.: 16/612,879

(22) PCT Filed: Oct. 20, 2017

(86) PCT No.: PCT/US2017/057640
§ 371 (c)(1),
(2) Date: Nov. 12, 2019

(87) PCT Pub. No.: WO2019/078887
PCT Pub. Date: Apr. 25, 2019

(65) Prior Publication Data
US 2020/0152302 A1    May 14, 2020

(51) Int. Cl.
*G16H 15/00*    (2018.01)
*G16H 10/60*    (2018.01)
(Continued)

(52) U.S. Cl.
CPC .............. *G16H 15/00* (2018.01); *G06N 20/00* (2019.01); *G16H 10/60* (2018.01); *G16H 70/20* (2018.01); *H04M 11/10* (2013.01)

(58) Field of Classification Search
CPC ........ G16H 15/00; G16H 10/60; G16H 70/20; G06N 20/00; H04M 11/10
See application file for complete search history.

(56) References Cited

U.S. PATENT DOCUMENTS

| | | | |
|---|---|---|---|
| 5,146,439 | A | 9/1992 | Jachmann et al. |
| 8,155,957 | B1 | 4/2012 | Takens |
| (Continued) | | | |

FOREIGN PATENT DOCUMENTS

| | | |
|---|---|---|
| CN | 106251865 A | 12/2016 |
| CN | 107038336 A | 8/2017 |
| (Continued) | | |

OTHER PUBLICATIONS

Savkov et al., Annotating patient clinical records with syntactic chunks and named entities: the Harvey Corpus, Lang. Resources & Evaluation (2016) 50:523-548.

(Continued)

*Primary Examiner* — Jason S Tiedeman
*Assistant Examiner* — Liza Tony Kanaan
(74) *Attorney, Agent, or Firm* — McDonnell Boehnen Hulbert & Berghoff LLP

(57) ABSTRACT

A method and system is provided for assisting a user to assign a label to words or spans of text in a transcript of a conversation between a patient and a medical professional and form groupings of such labelled words or spans of text in the transcript. The transcript is displayed on an interface of a workstation. A tool is provided for highlighting spans of text in the transcript consisting of one or more words. Another tool is provided for assigning a label to the highlighted spans of text. This tool includes a feature enabling searching through a set of predefined labels available for assignment to the highlighted span of text. The predefined labels encode medical entities and attributes of the medical (Continued)

entities. The interface further includes a tool for creating groupings of related highlighted spans of texts. The tools can consist of mouse action or key strokes or a combination thereof.

38 Claims, 19 Drawing Sheets

(51) Int. Cl.
*G16H 70/20* (2018.01)
*G06N 20/00* (2019.01)
*H04M 11/10* (2006.01)

(56) References Cited

U.S. PATENT DOCUMENTS

| | | | |
|---|---|---|---|
| 8,275,613 | B2 | 9/2012 | Harter et al. |
| 8,700,395 | B2 | 4/2014 | Zimmerman et al. |
| 8,783,396 | B2 | 7/2014 | Bowman |
| 9,348,818 | B2 | 5/2016 | Leydon et al. |
| 9,569,594 | B2 | 2/2017 | Casella dos Santos |
| 9,671,999 | B2 | 6/2017 | Guyott et al. |
| 9,679,107 | B2 | 6/2017 | Cardoza et al. |
| 9,697,192 | B1 | 7/2017 | Estes et al. |
| 9,824,691 | B1* | 11/2017 | Montero ............... G10L 15/26 |
| 10,390,082 | B2* | 8/2019 | Song .................... G06N 5/043 706/54 |
| 10,515,125 | B1* | 12/2019 | Lavergne ............... G06F 16/93 |
| 2003/0069877 | A1 | 4/2003 | Grefenstette ....... G06F 16/3323 |
| 2008/0115090 | A1 | 5/2008 | Disbrow |
| 2009/0198566 | A1* | 8/2009 | Greenberg ......... G06Q 30/0236 707/727 |
| 2010/0312725 | A1* | 12/2010 | Privault ................ G06N 5/043 706/54 |
| 2013/0080161 | A1 | 3/2013 | Iwata et al. |
| 2014/0142962 | A1* | 5/2014 | Bhatt ..................... G16H 15/00 705/2 |
| 2014/0236580 | A1 | 8/2014 | Peters |
| 2015/0134362 | A1* | 5/2015 | Schneider ............ G16H 40/20 705/3 |
| 2015/0379212 | A1* | 12/2015 | Kaukab ................. G16H 40/20 705/3 |
| 2016/0162458 | A1* | 6/2016 | Munro ................ G06F 16/285 715/230 |
| 2017/0147758 | A1 | 5/2017 | Gupta et al. |
| 2019/0213755 | A1* | 7/2019 | Bassa ..................... G06V 20/58 |

FOREIGN PATENT DOCUMENTS

| | | |
|---|---|---|
| JP | 2005-267358 A | 9/2005 |
| JP | 2007-58715 A | 3/2007 |
| JP | 2011-204249 A | 10/2011 |
| JP | 2013-72974 A | 4/2013 |
| WO | 2005/050474 A2 | 6/2005 |

OTHER PUBLICATIONS

Klann et al., An intelligent listening framework for capturing encounter notes from a doctor-patient dialog BMC Medical Informatics and Decision Making 2009 9 (Suppl 1): 53.

Seid Muhie Yimam et al, "WebAnno: A Flexible, Web-based and Visually Supported System for Distributed Annotations", Proceedings of the 51st Annual Meeting of the Association for Computational Linguistics, Sep. 4, 2013, pp. 1-6.

WebAnno User Guide, Feb. 23, 2017, pp. 1-66, URL:https://webanno.github.io/webanno/releases/3.2.2/docs/user-guide.

WebAnno: "WebAnno 2 Tutorial—02—Annotation and Curation", Aug. 9, 2014, XPO54978385, Retrieved from the Internet: URL:https://222.youtube.com/w2atch?v-sQ5pFoFzxlk&t=128s.

Seid Muhie Yimam et al, "Automatic Annotation Suggestions and Custom Annotation Layers in WebAnno", Proceedings of 52nd Annual Meeting of the Association for Computational Linguistics: System Demonstrations, Jun. 24, 2014, pp. 91-96.

Stenetorp et al, "BRAT: a Web-based Tool for NLP-Assisted Text Annotation", Proceedings of the 13th Conference of the European Chapter of the Association for Computational Linguistics, Apr. 23, 2012, pp. 102-107.

Configuration—brat rapid annotation tool, Oct. 3, 2017, XP055479682, retrieved from internet: URL:https//web.archive.org/web/20171003110037/http:brat.nlplab.org/configuration.html.

Kaplan et al, "Slate—a tool for creating and maintaining annotated corpora", J. Lang. Technol. Comput. Linguisti., Oct. 31, 202, pp. 91-103, XP055479314, retrieved from the internet: URL:http://www.jlcl.org/2011_Heft2/11.pdf.

Yimam et al, "An adaptive annotation approach for biomedical entity and relation recognition", Brain Informatics, vol. 3, No. 3, Feb. 27, 2016, pp. 157-168, XP055478856.

International Search Report and Written Opinion for PCT/US2017/057640 dated Jun. 27, 2018, 20 pages.

Japanese Office Action (with English translation) from the Japanese Patent Office, for Japanese Patent Application No. 2019-566258, dated Jan. 18, 2021, pp. 1-12.

Torii, Kentaro et al., "Voice Tweet SNS for Home Medical Care Services to Support Communication among Healthcare Staff", Toshiba Review, Toshiba Corporation, Nov. 1, 2014, vol. 69, No. 11, pp. 22-25. [No English version available].

Yimam et al. "WebAnno: A Flexible, Web-based and Visually Supported System for Distributed Annotations" DOI: https://www.aclweb.org/anthology/P13-4001.pdf.

Stenetorp et al. "BRAT: a Web-based Tool for NLP-Assisted Text Annotation" DOI: https://www.aclweb.org/anthology/E12-2021.pdf.

Proview Practice Series Global User Guide, Thomson Reuters.

WebAnno User Guides, The WebAnno Team, Version 2.3.0 (retrieved May 12, 2021).

A Method for Extracting Missed Information of Twitter based on a Topic Graph Considering Duration of Viewing, IPSJ SIG Technical Report (DBS, IPSG, Nov. 19, 2015, pp. 1 to 8) (No English version available).

* cited by examiner

Conversation: 3     Interaction: Abdominal Discomfort 0.75x   Normal   1.15x   1.5x

△ 0:00

1 Dr   Hi Miss Elin, it's a pleasure to meet you. I'm Dr. Alyin.
2 Pt   Good to meet you.
3 Dr   Well, welcome. First, I know Yumi asked you a bunch of questions. She told me a little bit about it. I know it's a little annoying , but I want to hear it for myself, exactly what's bveen going on. So what brings you to the clinic?
4 Pt   Well, I do have a bit of a stomachache and it's been bothering me, I think, for three days That's what I finally thought I should come in. It's sort of, you know- - not life-threatening. It doesn't feel that way. But it's really bugging me.
5 Dr   Oh, sorry. Tell me more about it.
6 Pt   It's a little up here, in the upper left. I'm very bad at -- and it's sort of on and off, but it's very much after I've been eating. And several hours after. Perhaps it's just digestive movement that are irritating something/
7 Dr   And have you had digestive problems in the past?
8 Pt   No.
9 Dr   Okay. So, prior to three days ago, you were feeling okay, feeling like your normal self?
10 Pt   Yes, my normal self is pretty good. Yeah, yeah, I have a little asthma, I think she also told you. And that's -- I think -- well controlled.
11 Dr   Okay, fantastic. Great to hear that. And so, is it out of the blue, all of a sudden, that you started having this pain? When's the first time you noticed it?
12 Pt   Well, you know, I -- it's very hard to say, because I just moved, and everything

FIG. 2
| A | B |
| C | D |

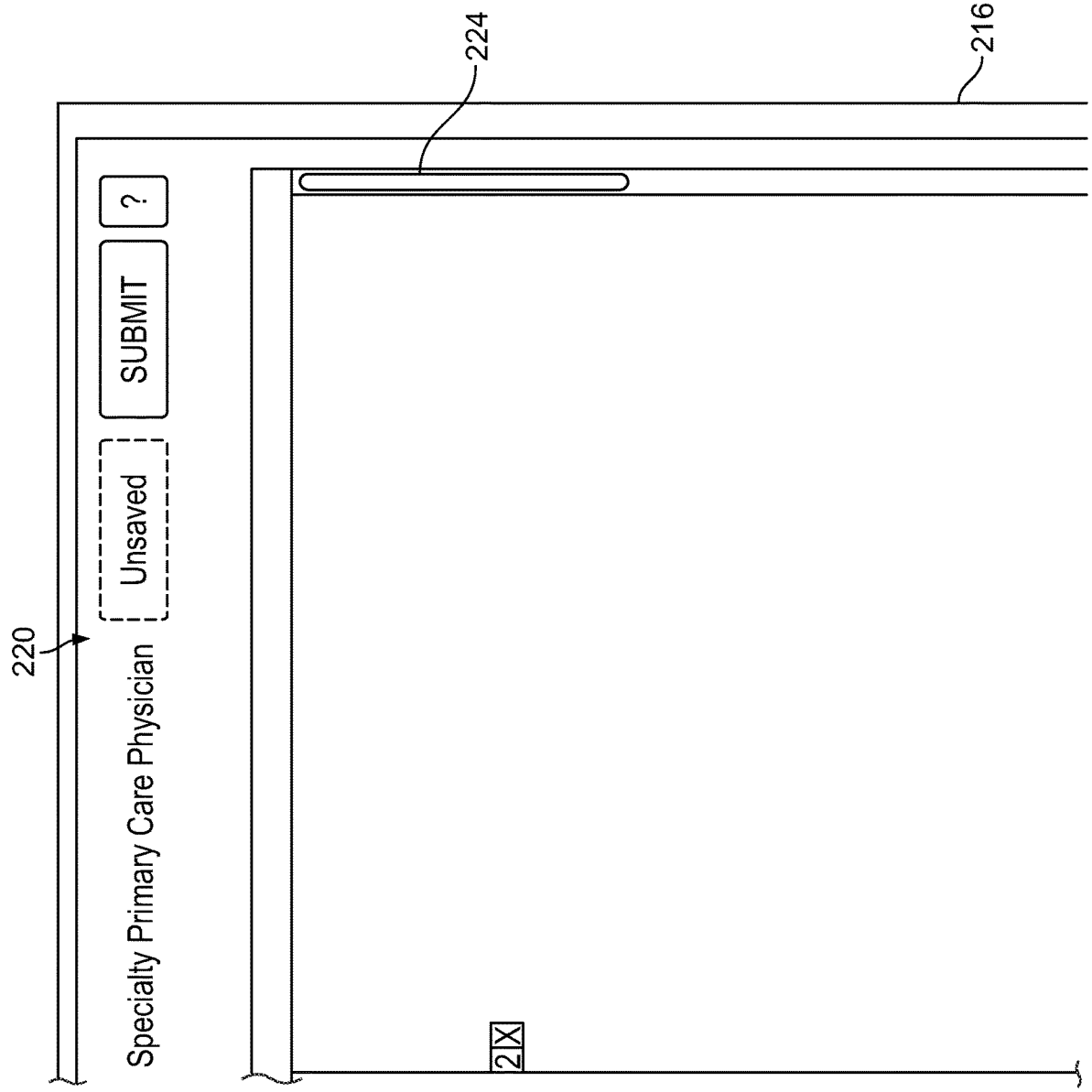

has been up in chaos for the last --
13 Dr Stressful
14 Pt Yeah. So I think that -- I don't know why it came. I know that I started noticing it three days age.
15 Dr Got it. And when you get it, does it start all of a sudden, or does it kind of slowly come on?
16 Pt It's actually sudden. "Ugh" and then I have this discomfort. And it is after a meal. And I've tried to then be careful about what I ear, and that's something that requires heavy digestive effort, but it doesn't seem to be something that I can control.
17 Dr So, is it true that some foods cause it and some foods don't cause it?
18 Pt No, that's what I'm saying -- it doesn't seem to --
19 Dr It's hard to tell. Okay. And is it after every meal or after one meal in particullar?
20 Pt I think it's primarily -- it's worse in the morning, and then, perhaps I'm not noticing it as much in dinner because tehn we have conversation, my husband and I are sitting, talking about everything, and so I'm nicely distracted.

| TABLE | GROUPS | |
|---|---|---|
| | location | snippets |
| | 4 | (stomachache) (three days) |

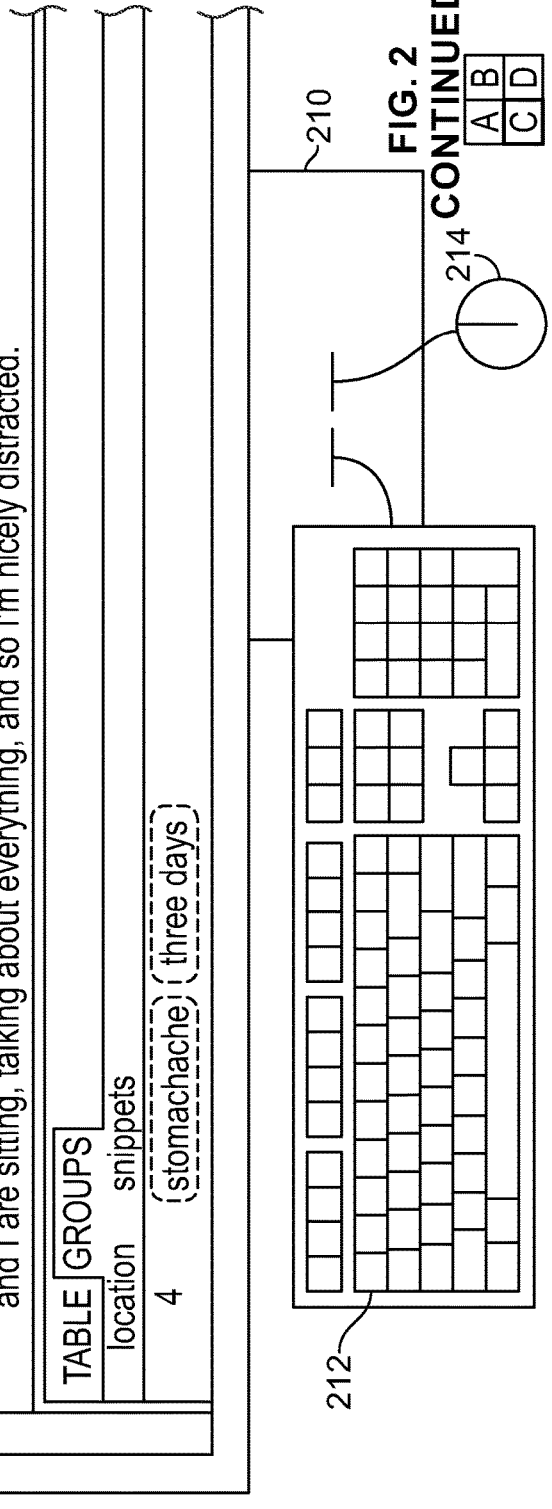

FIG. 2 CONTINUED

| | | | | |
|---|---|---|---|---|
| ▽TODO - 20 tasks | | | | |
| 1 | 20994 | 10:01 218 | Abdominal Discomfort | Primary Care - Initial Visit |
| | | 20:01 73 | Gastroesophageal Reflux Disease (GERD) | Primary Care Physican |
| 3 | 14155 | 10:01 89 | Abdominal Discomfort | Primary Care Physican |
| | 23989 | 30:01 242 | Menopause | Primary Care Physican |
| | 25277 | 20:01 37 | Well Visit | Primary Care Physican |
| | 29748 | 10:01 90 | Type II Diabetes | Primary Care Physican |
| | 33271 | 22:01 246 | Type II Diabetes | Primary Care Physican |
| | 37709 | 10:01 81 | Dyslipidemia | Primary Care Physican |
| | 42932 | 40:01 435 | Patients taking Opioids | Primary Care Physican |
| | 49577 | 20:01 135 | COPD | Primary Care Physican |
| | 84761 | 20:01 132 | Migraine | Primary Care Physican |
| | 99868 | 30:01 340 | Type II Diabetes | Primary Care Physican |
| 2 | | 5:01 66 | Venous Thrombo-Embolism | Primary Care Physican |
| | 1011775 | 6:01 44 | Abdominal Discomfort | Primary Care Physican |
| | 51854 | 10:01 125 | Type II Diabetes | Primary Care Physican |
| | 103516 | 20:01 192 | Type II Diabetes | Primary Care Physican |
| | 106338 | 30:01 297 | Type II Diabetes | Primary Care Physican |
| 4 | | 20:01 268 | Type II Diabetes | Primary Care Physican |
| 5 | | 6:01 44 | Abdominal Discomfort | Primary Care Physican |
| | | 8:01 89 | Abdominal Discomfort | Primary Care Physican |
| ▽ Completed - 2 tasks | | | | |
| 1 | | 20:01 218 | Abdominal Discomfort | Primary Care - Initial Visit  6/8/2017, 3:42:42 PM |

Conversation: 3    Interaction: Abdominal Discomfort 0.75x  1.15x  1.5x
[Normal]
▷ 0:00

1 Dr   Hi Miss Elin, it's a pleasure to meet you. I'm Dr. Alyin.
2 Pt   Good to meet you.
3 Dr   Well, welcome. First, I know Yumi asked you a bunch of questions. She told me a little bit about it. I know it's a little annoying , but I want to hear it for myself, exactly what's bveen going on. So what brings you to the clinic?
4 Pt   Well, I do have a bit of a [stomachache] and it's been bothering me, I think, for [three days] That's what I finally thought I should come in. It's sort of, you know- - not life-threatening. It doesn't feel that way. But it's really bugging me.
5 Dr   Oh, sorry. Tell me more about it.
6 Pt   It's a little up here, in the [upper left]. I'm very bad at -- and it's sort of on and off, but it's very much after I' [x] hours after. Perhaps it's just digestive movement that are irritating something/
7 Dr   And have you had digestive/problems in the past?
8 Pt   No.
9 Dr   Okay. So, prior to three days ago, you were feeling okay, feeling like your normal self?
10 Pt  Yes, my normal self is pretty good. Yeah, yeah, I have a little asthma, I think she also told you. And that's -- I think -- well controlled.
11 Dr  Okay, fantastic. Great to hear that. And so, is it out of the blue, all of a sudden, that you started having this pain? When's the first time you noticed it?

FIG. 4
| A | B |
| C | D |

12 Pt Well, you know, I -- it's very hard to say, because I just moved, and everything has been up in chaos for the last --
13 Dr Stressful
14 Pt Yeah. So I think that -- I don't know why it came. I know that I started noticing it three days age.
15 Dr Got it. And when you get it, does it start all of a sudden, or does it kind of slowly come on?
16 Pt It's actually sudden. "Ugh" and then I have this discomfort. And it is after a meal. And I've tried to then be careful about what I ear, and that's something that requires heavy digestive effort, but it doesn't seem to be something that I can control.
17 Dr So, is it true that some foods cause it and some foods don't cause it?
18 Pt No, that's what I'm saying -- it doesn't seem to --
19 Dr It's hard to tell. Okay. And is it after every meal or after one meal in particullar?
20 Pt I think it's primarily -- it's worse in the morning, and then, perhaps I'm not noticing it as much in dinner because tehn we have conversation, my husband and I are sitting, talking about everything, and so I'm nicely distracted.

410

| TABLE | GROUPS | | | | |
|---|---|---|---|---|---|
| tag | | | | location | text |
| Sym | GI | | Abdominal Pain | 4 | stomachache |
| SymAttr | Duration | | | 4 | three days |
| | Medical Entity | | Attribute | | |

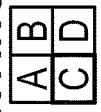

FIG. 4
CONTINUED

Conversation: 3                Interaction: Abdominal Discomfort 0.75x [Normal]  1.15x   1.5x

△ 0:00 ▢————————————————————

1 Dr  Hi Miss Elin, it's a pleasure to meet you. I'm Dr. Alyin.
2 Pt  Good to meet you.
3 Dr  Well, welcome. First, I know Yumi asked you a bunch of questions. She told me a little bit about it. I know it's a little annoying , but I want to hear it for myself, exactly what's bveen going on. So what brings you to the clinic?
4 Pt  Well, I do have a bit of a [stomachache] and it's been bothering me, I think, for [three days] That's what I finally thought I should come in. It's sort of, you know- - not life-threatening. It doesn't feel that way. But it's really bugging me.
5 Dr  Oh, sorry. Tell me more about it.
6 Pt  It's a little up here, in the [upper left.] I'm very bad at -- and it's sort of on and off, but it's very much after I' [SymAttr:Location (on body)] x [X] hours after. Perhaps it's just digestive movement that/are irritating something/ ~504
            502
7 Dr  And have you had digestive/problems in the past?
8 Pt  No.
9 Dr  Okay. So, prior to three days ago, you were feeling okay, feeling like your normal self?
10Pt  Yes, my normal self is pretty good. Yeah, yeah, I have a little asthma, I think she also told you. And that's -- I think -- well controlled.

FIG. 5
| A | B |
| C | D |

Specialty Primary Care Physician    Last saved at 10:47:50    SUBMIT    ?

Search tags, e.g. tobacco currfreq <ESC> to quit

2|X|
NOS
SymAttr:Time of Onset
SymAttr:Frequency/Tempo
SymAttr:Duration
SymAttr:Improving Worsening
SymAttr:Location (on body)
SymAttr:Severity/Amount
SymAttr:Characteristic/Quality
SymAttr:Provoking Factor
SymAttr:Radiation
SymAttr:Not Experienced
SymAttr
Chief Complaint
Meds
Meds:Physician's Intended Status:
Meds:Physician's Intended Status:Active, Continued
Meds:Physician's Intended Status:Active, Modified

FIG. 5
CONTINUED
| A | B |
| C | D |

11 Dr  Okay, fantastic. Great to hear that. And so, is it out of the blue, all of a sudden, that you started having this pain? When's the first time you noticed it?

12 Pt  Well, you know, I -- it's very hard to say, because I just moved, and everything has been up in chaos for the last --

13 Dr  Stressful

14 Pt  Yeah. So I think that -- I don't know why it came. I know that I started noticing it three days age.

15 Dr  Got it. And when you get it, does it start all of a sudden, or does it kind of slowly come on?

16 Pt  It's actually sudden. "Ugh" and then I have this discomfort. And it is after a meal. And I've tried to then be careful about what I ear, and that's something that requires heavy digestive effort, but it doesn't seem to be something that I can control.

17 Dr  So, is it true that some foods cause it and some foods don't cause it?

18 Pt  No, that's what I'm saying -- it doesn't seem to --

19 Dr  It's hard to tell. Okay. And is it after every meal or after one meal in particullar?

20 Pt  I think it's primarily -- it's worse in the morning, and then, perhaps I'm not noticing it as much in dinner because tehn we have conversation, my husband and I are sitting, talking about everything, and so I'm nicely distracted.

410

506

| TABLE | GROUPS | | | |
|---|---|---|---|---|
| tag | | | location | text |
| Sym | GI | Abdominal Pain | | |
| SymAttr | Duration | | 4 | stomachache |
| SymAttr | Location (on body) | | 4 | three days |
| | | | 6 | upper left |

FIG. 5
CONTINUED

| A | B |
|---|---|
| C | D |

Conversation: 3    Interaction: Abdominal Discomfort 0.75x [Normal] 1.15x 1.5x

△ 0:00 ▭

1 Dr  Hi Miss Elin, it's a pleasure to meet you. I'm Dr. Alyin.
2 Pt  Good to meet you.
3 Dr  Well, welcome. First, I know Yumi asked you a bunch of questions. She told me a little bit about it. I know it's a little annoying , but I want to hear it for myself, exactly what's bveen going on. So what brings you to the clinic?
4 Pt  Well, I do have a bit of a [stomachache] and it's been bothering me, I think, for [three days] That's what I finally thought I should come in. It's sort of, you know- - not life-threatening. It doesn't feel that way. But it's really bugging me.
5 Dr  Oh, sorry. Tell me more about it.
6 Pt  It's a little up here, in the upper left. I'm very bad at -- and it's sort of on and off, but it's very much after I've been eating. And several hours after. Perhaps it's just digestive movement that are irritating something/
7 Dr  And have you had digestive problems in the past?
8 Pt  No.
9 Dr  Okay. So, prior to three days ago, you were feeling okay, feeling like your normal self?
10 Pt Yes, my normal self is pretty good. Yeah, yeah, I have a little asthma, I think she also told you. And that's --1 think -- well controlled.

FIG. 6
| A | B |
| C | D |

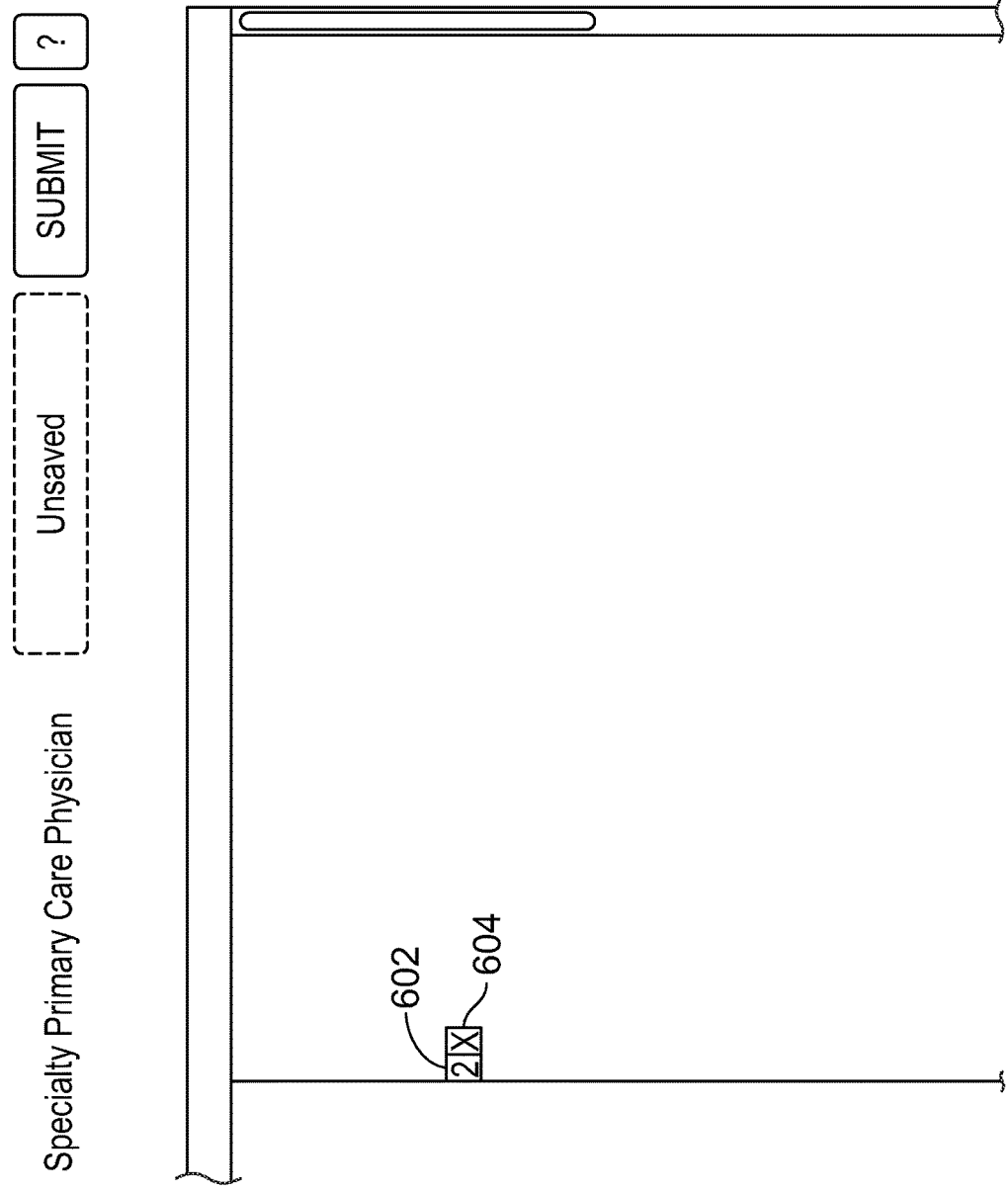

11 Dr  Okay, fantastic. Great to hear that. And so, is it out of the blue, all of a sudden, that you started having this pain? When's the first time you noticed it?

12 Pt  Well, you know, I -- it's very hard to say, because I just moved, and everything has been up in chaos for the last --

13 Dr  Stressful

14 Pt  Yeah. So I think that -- I don't know why it came. I know that I started noticing it three days age.

15 Dr  Got it. And when you get it, does it start all of a sudden, or does it kind of slowly come on?

16 Pt  It's actually sudden. "Ugh" and then I have this discomfort. And it is after a meal. And I've tried to then be careful about what I ear, and that's something that requires heavy digestive effort, but it doesn't seem to be something that I can control.

17 Dr  So, is it true that some foods cause it and some foods don't cause it?

18 Pt  No, that's what I'm saying -- it doesn't seem to --

19 Dr  It's hard to tell. Okay. And is it after every meal or after one meal in particullar?

20 Pt  I think it's primarily -- it's worse in the morning, and then, perhaps I'm not noticing it as much in dinner because tehn we have conversation, my husband and I are sitting, talking about everything, and so I'm nicely distracted.

| TABLE | GROUPS | |
|---|---|---|
| location | snippets | |
| 4 | {stomachache} | {three days} |
|   | 608 | 606 |

FIG. 6 CONTINUED
| A | B |
| C | D |

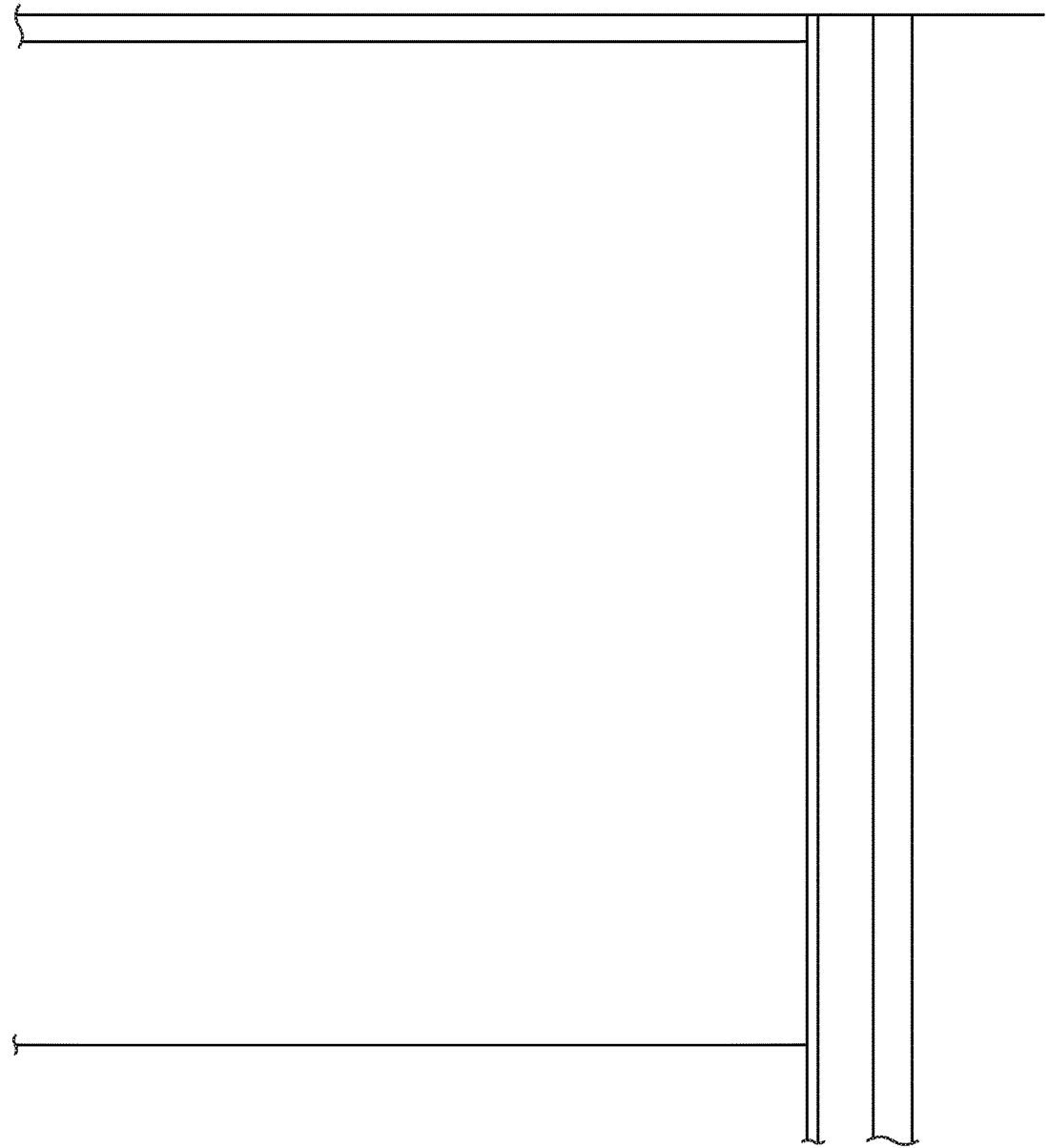

CAPTURING DETAILED STRUCTURE FROM PATIENT-DOCTOR CONVERSATIONS FOR USE IN CLINICAL DOCUMENTATION

CROSS-REFERENCE TO RELATED APPLICATION

The present application is a national stage entry of PCT/US2017/057640 filed Oct. 20, 2017, the contents of which is hereby incorporated by reference.

BACKGROUND

This disclosure is directed to a method and system for facilitating the annotation of transcribed audio or audio-visual recordings of medical encounters.

Conversations between patients and medical practitioners such as doctors and nurses and their conversations are often recorded. The record of the conversation, and a transcript, are part of the patient's medical record. The transcript can be created by a speech-to-text converter or created by a trained (human) medical transcriptionist listening to the recording.

A transcript without any annotation is of limited usefulness when it is reviewed by the physician, as they have to pore over many lines or pages of the transcript to find relevant information or understand the relatedness of different comments in the transcript.

Additionally, a collection of transcripts of medical encounters can be used to train machine learning models. Training a machine learning model requires a large amount of high quality training examples, i.e., labelled data. There is a need in the art for methods for facilitating the generation of transcripts of medical encounters that are annotated, that is, relevant words or phrases are highlighted and associated with medical concepts and grouped as being related to each other. This disclosure meets that need.

SUMMARY

In a first aspect, a method of facilitating annotation of a recording of a medical practitioner-patient conversation is disclosed. The method includes a step of generating a display of the transcribed audio recording (i.e., transcript), for example on the display of a workstation used by a human ("scribe labeler") who is performing the annotation. A tool is provided for highlighting spans of text in the transcript consisting of one or more words. The tools can be simple mouse or keyboard shortcuts for selecting or highlighting one or more words.

The method further includes a step of providing a tool for assigning a label to the highlighted spans of text. The tool includes a feature for searching through a set of predefined labels available for assignment to the highlighted span of text. For example, when the scribe labeler highlights a word such as "stomachache" in the transcript a window pops up where the user can search through available labels, e.g. by scrolling or using a search tool. The labels encode medical entities (such as symptoms, medications, lab results, etc.) and attributes of the medical entities (e.g., severity, location, frequency, time of onset of a symptom entity).

In this document, the term "medical entities" is intended to refer to categories of discrete medical topics, such as symptoms, medications, lab results, vital signs, chief complaint, medical imaging, conditions, medical equipment, and so forth. The medical entities are predefined to be relevant to the context of the labelling task, and so in this case in one embodiment they could consist of the following list: medications, procedures, symptoms, vitals, conditions, social history, medical conditions, surgery, imaging, provider, vaccine, reproductive history, examination, and medical equipment. The medical entities could be structured in a hierarchical manner, such as the medical entity "medication" could be in the form of "medication:allergy" where "allergy" is a type or subclass of the overall class "medication." As another example, the medical entity "symptom" could be structured in a hierarchical manner of symptoms for different parts of the body, such as "symptom:eyes", "symptom:neurological", etc.

The term "attributes of the medical entities" simply means some descriptive property or characteristic of the medical entity, such as for example the medical entity "medical equipment" may have an attribute of "patient's actual use" meaning that the patient is currently using a piece of medical equipment. As another example, a symptom medical entity may have an attribute of "onset." A label of "symptom/onset" would be used as an annotation when there is word or phrase in the transcript indicating when the patient first started experiencing the symptom. As another example, a label of "medical equipment/regularly" would be used as an annotation when there is a word or phrase in the transcript indicating the patient used some piece of medical equipment regularly, with "regularly" being the attribute of the medical entity "medical equipment."

The method further includes a step of providing a tool for grouping related highlighted spans of texts. The tool could be for example a combination of mouse clicks or keyboard shortcuts to establish the grouping. The groupings allow medical entities associated with labels assigned to the highlighted spans of text to be associated as a group. For example, in a conversation in which a patient describes a sharp chest pain that started last week, the text "sharp", "chest pain" and "last week" would be highlighted and labeled with symptom labels and attributes of severity, location, and time of onset, respectively and grouped together as all being related to each other.

In another aspect, a system is disclosed for facilitating annotation of a recording of a medical practitioner-patient conversation. The system includes a) an interface displaying a transcript of the recording; b) a tool for highlighting spans of text in the transcript consisting of one or more words; c) a tool for assigning a label to the highlighted spans of text, wherein the tool includes a feature enabling searching through predetermined labels available for assignment to the highlighted span of text, and wherein the labels encode medical entities and attributes of the medical entities; and d) a tool for creating groupings of related highlighted spans of texts.

The methods and systems are applicable to other types of transcripts, in which a set of predefined labels are created, e.g., by an operator, which are designed to be relevant to the annotation task at hand and the labels are associated with entities and attributes relevant to the transcript and annotation task. The tools of this disclosure are used in the same manner in these other possible implementations, such as for example transcripts of legal proceedings, such as deposition or trial, or transcripts of hearings before administrative bodies, such a city council, Congress, State Legislature, etc.

BRIEF DESCRIPTION OF THE DRAWINGS

FIG. 3 is an illustration of the user interface of FIG. 2 showing a list of transcripts which are ready for annotation.

FIG. 4 shows a search box which pops up which permits the scribe labeler to search for medical entities and associated attributes. Spans of text can be highlighted by use of a tool such as by clicking on the word or using drag techniques with a mouse.

FIG. 6 is illustration of the transcript of FIGS. 4 and 5 when the scribe labeler forms a grouping of the two highlighted spans of text "stomachache" and "three days". The tool for forming the grouping consists of a highlighting the two texts and then keyboard shortcut of holding down the "G" key, clicking on the highlighted spans of text, and releasing the "G" key. FIG. 6 also shows the formation of the group in the Groups tab listing all the groups in the transcript at the bottom of the display.

DETAILED DESCRIPTION

This disclosure is directed to methods and systems for facilitating annotations of recordings of medical encounters, i.e., conversations between patients and medical practitioners such as doctors or nurses. The recordings could be audio or audio-visual recordings. The recordings are transcribed into written form. The transcripts could be generated by trained medical transcriptionists, that is by hand, or by the use of speech to text converters, which are known in the art. The output of the system is an annotated version of the transcript in which relevant medical information (i.e., spans of text, such as individual words or groups of words) in the text are labeled (i.e., tagged as being associated with medical entities and attributes of such entities), and grouped to express relatedness between the labelled text.

Figure 1:
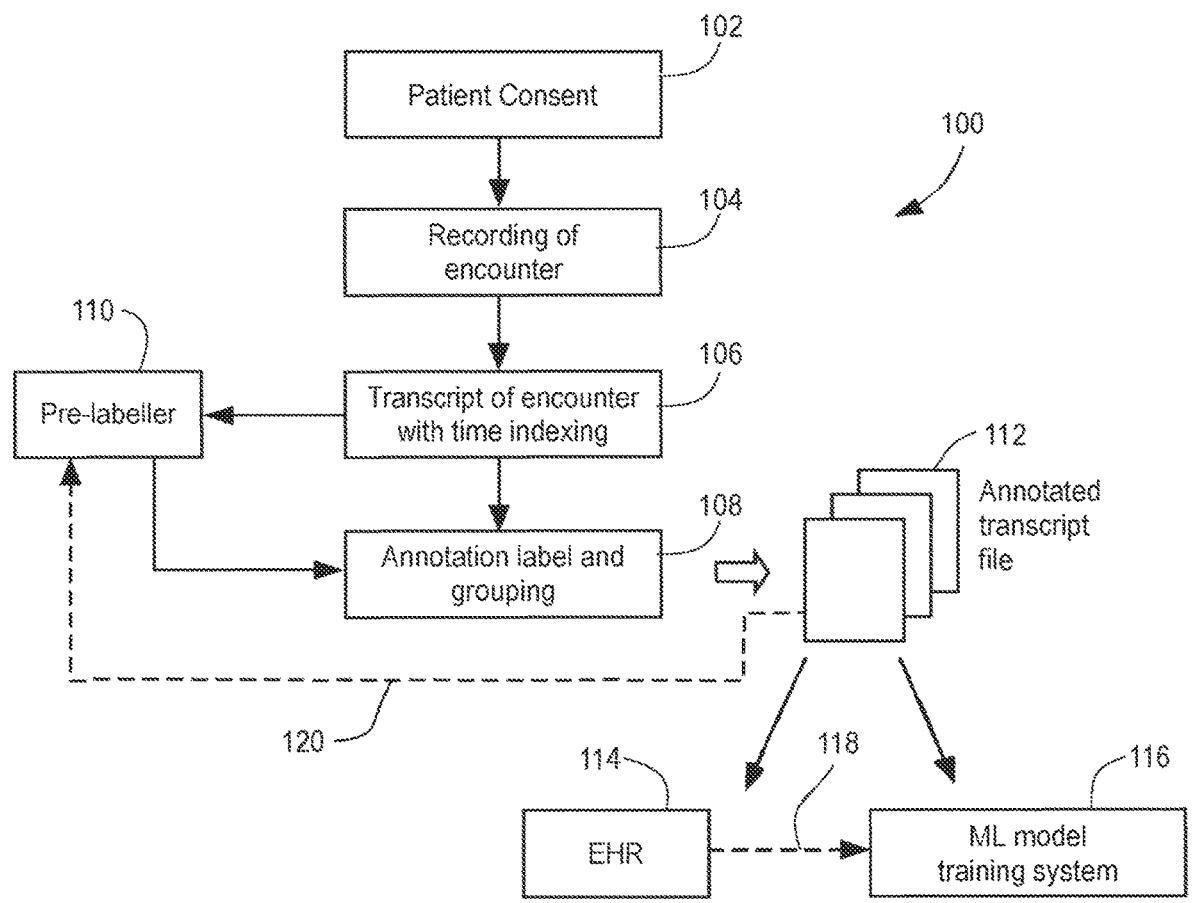
FIG. 1 is a flow chart showing an environment in which the method can be performed.

FIG. 1 is a flow chart showing the environment in which the methods and systems of this disclosure are practiced. Patient consent for recording the encounter with the doctor or nurse is obtained at 102. Additionally, the patient is advised of the use of a transcript of the recording to be placed into the electronic health record and consent is obtained. The patient is further advised that the recording may be annotated and used for generating or training machine learning models and consent is obtained as well. In all cases where the transcripts are annotated or used for machine learning model training the transcript data is patient de-identified and used in compliance with all requirements for disclosure and use of a limited data set under HIPAA. Ethics review and institutional review board exemption is obtained from each institution. Patient data is not linked to any Google user data. Furthermore, for the system 116 using annotated transcripts for machine learning model training includes a sandboxing infrastructure that keeps each electronic health record (or transcript) dataset separated from each other, in accordance with regulation, data license and/or data use agreements. The data in each sandbox is encrypted; all data access is controlled on an individual level, logged, and audited.

At step 104, after the required patient consents are obtained, the patient consults with the medical practitioner and a recording, either audio or audio-visual, is obtained and stored in digital format.

At step 106, a written transcript of the recording is obtained, either by a trained transcriptionist or by use of a speech-to-text converter. The transcript is preferably accompanied by a time indexing, in which the words spoken in the transcript, or lines of text, are associated with elapsed time of the recording, as will be illustrated subsequently.

At step 108, an annotation of the transcript is performed by the scribe labeler in the manner described and explained in the subsequent figures. The annotations include the assignment of labels to spans of text in the transcript and groupings of spans of text to indicate their relatedness. In step 108 a display of the transcribed audio recording is generated, for example on the display of a workstation used by the scribe labeler. See FIGS. 2 and 4-6. A tool is provided for highlighting spans of text in the transcribed audio recording consisting of one or more words. The tool can be simple mouse or keyboard shortcuts for selecting or highlighting one or more words. A tool is also provided for assigning a label to the highlighted spans of text. The tool includes a feature for searching through predetermined labels available for assignment to the highlighted span of text. For example, when the scribe labeler highlights a word such as "stomachache" in the transcript a list pops up where the user can search through available labels, and a search tool is provided for performing a word search through the list of labels. The labels encode medical entities (such as symptoms, medications, lab results, etc.) and attributes of the medical entities (e.g., severity, location, frequency, time of onset of a symptom entity).

A tool is also provided for grouping related highlighted spans of texts. The groupings allow medical entities associated with labels to be grouped together. For example, in a conversation in which a patient describes a sharp chest pain that started last week, the text "sharp", "chest pain" and "last week" would be highlighted and labeled with symptom labels and attributes of severity, location, and time of onset, and grouped together, as they are all related to a single medical condition of the patient. This tool can consist of keyboard and/or or mouse action, as explained below.

Figure 7:
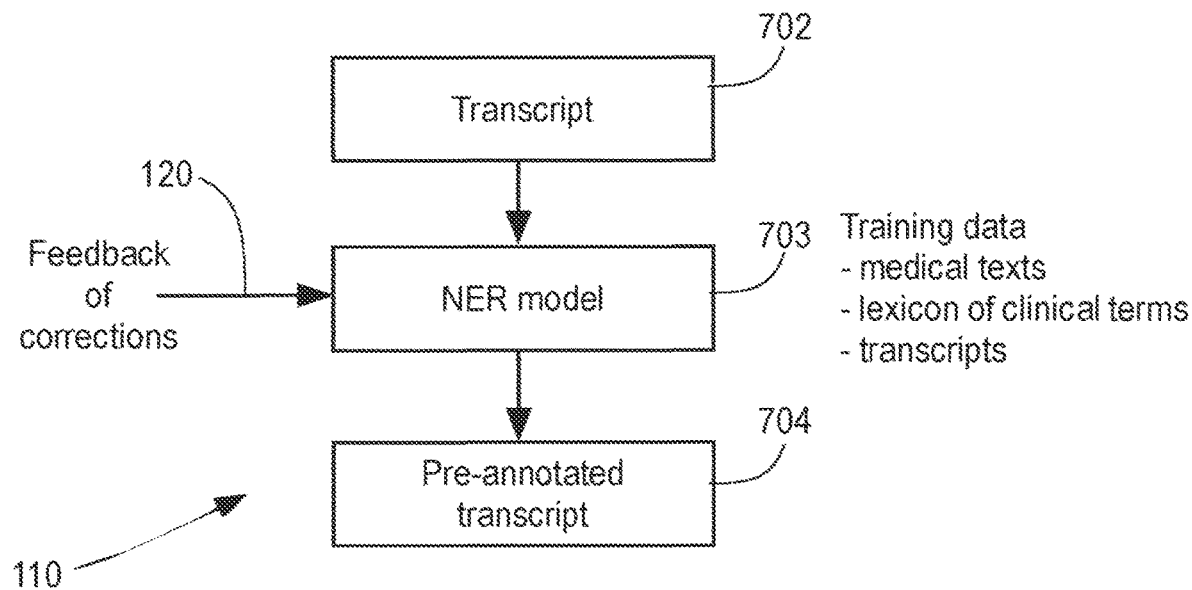
FIG. 7 is a more detailed illustration of the pre-labeler of FIG. 1.

The system may include a pre-labeler 110, shown in more detail in FIG. 7. The pre-labeler is a computer system implementing a learned, automated word recognition model which identifies words or spans of text in the transcript which are likely to be the subject of labelling or grouping. The pre-labeler 110 provides input into annotation step 108 by providing suggested labels for highlighted spans of text when the scribe labeler performs the annotation of the transcript. This is shown in more detail in FIG. 5.

As a result of the annotation step 108 an annotated transcript file 112 is created, which consists of the transcript as well as annotations in the form of labelled or tagged spans of text (words or phrases) and groupings of the tagged spans of text. The annotated transcript file is in digital form, with the annotations and groupings in the file as metadata or otherwise. The annotated transcript file 112 is then added to the patient's electronic health record (EHR) 114 or supplied to a machine learning model training system 116. The machine learning model training system 116 may, for example, be a system for training a machine learning model to automatically annotate transcripts of medical encounters. Alternatively, the machine learning model may use the annotated transcript as well as other data in the patient health record, for not only the individual patient, but also a multitude of other patients, to generate predictions of future medical events for example as described in the U.S. provisional application Ser. No. 62/538,112 filed Jul. 28, 2017, the content of which is incorporated by reference herein. The EHR 114 may be provided to the system 116 as indicated by the dashed line 114.

The annotated transcript file 112 may be fed back into the pre-labeler to enable further training the machine learning pre-labeler 110, as indicated by the dashed line 120. This aspect will be described in further detail later.

Figure 2:
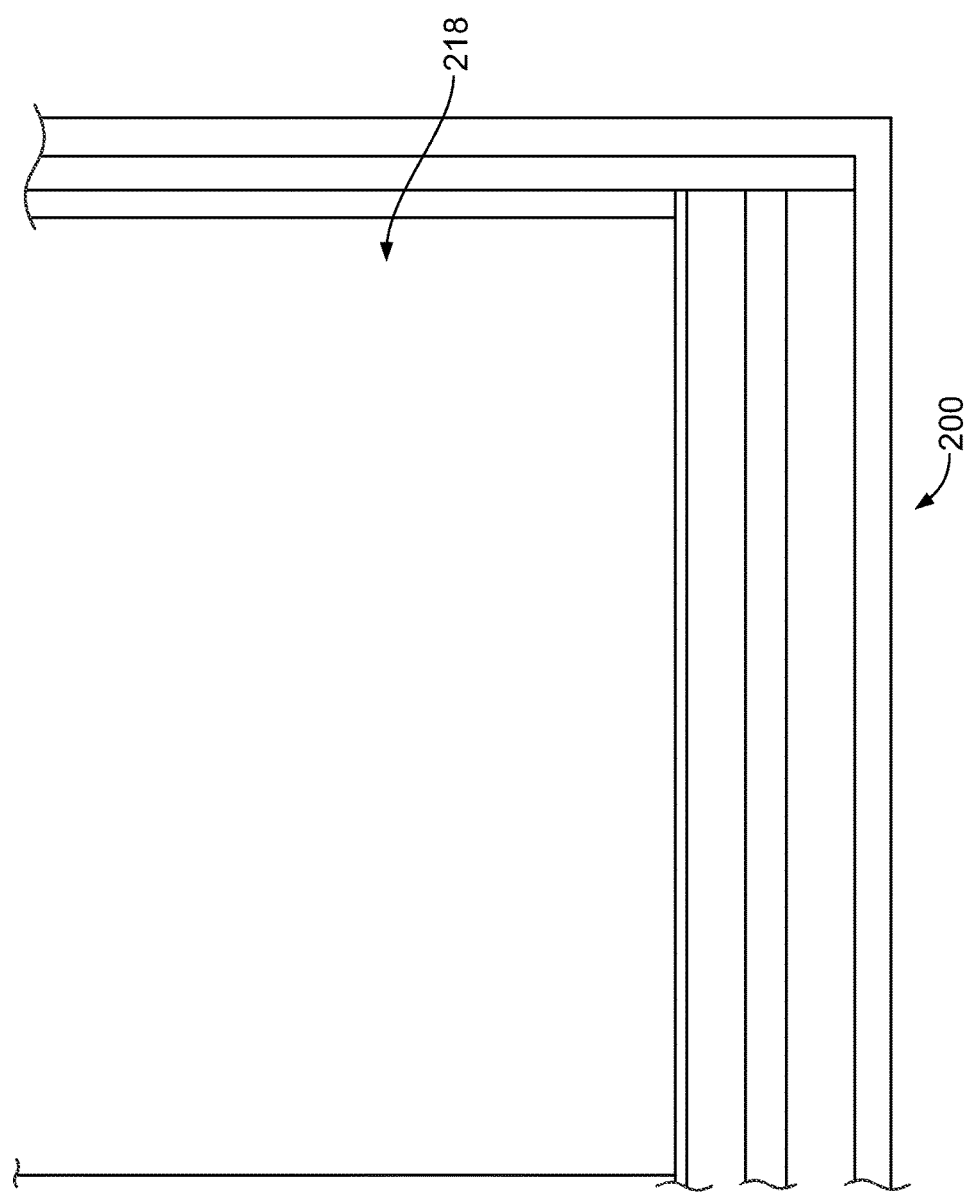
FIG. 2 is an illustration of workstation having a display and user interface for use by a human ("scribe labeler") to annotate a transcript of medical encounter. The user interface includes the tools described in conjunction with FIGS. 4-6. The term "user interface" is intended to refer to the combination of the display on the workstation and associated devices for providing user input, such as the mouse and keyboard.

FIG. 2 is an illustration of a workstation 200 which is used by a scribe labeler during the annotation step 108 of FIG. 1. The workstation includes a central processing unit (general purpose computer 210) executing an application which provides for display of the transcript of the medical encounter and tools by which the user interface consisting of a keyboard 212, a mouse 214 and a monitor 216 allow for the highlighting of spans of text (words or phrases 230), assigning labels to the spans of text, and grouping of the highlighted spans of text as will be discussed below. The monitor 216 includes a display 218 of a transcript 222, and a scroll bar 224 for allowing the user to navigate to various portions of the transcript. A time index 220 of the transcript is shown at the top of the display 218. The time index includes a slider 221 which when moved horizontally back and forth allows for the portion of the transcript associated with a particular elapsed time to be displayed at the top of the display 118. In this case the time index 220 indicates that the transcript is 13 minutes 24 seconds duration and the slider 221 is all the way to the left, therefore the beginning of the transcript is shown at the top of the display. The transcript is in the form of numbered lines, followed by identification of who was speaking (doctor or patient), followed by a text transcript of what was said.

FIG. 3 shows the display of a "to-do" list of transcripts in need of annotation which is provided on the user interface of FIG. 2 when the scribe labeler logs on to the workstation of FIG. 2. The individual transcripts are patient de-identified (that is, identified only by patient number in column 302 and not by name). Column 304 shows the elapsed time, column 306 shows the number of lines of text in the transcript, column 308 shows the patient's chief complaint associated with the medical encounter, and column 310 shows the nature or type of the medical encounter. When one of the transcripts is selected in FIG. 3 (e.g., by clicking on the number in the column 302) the display of FIG. 2 is generated.

Figure 4:
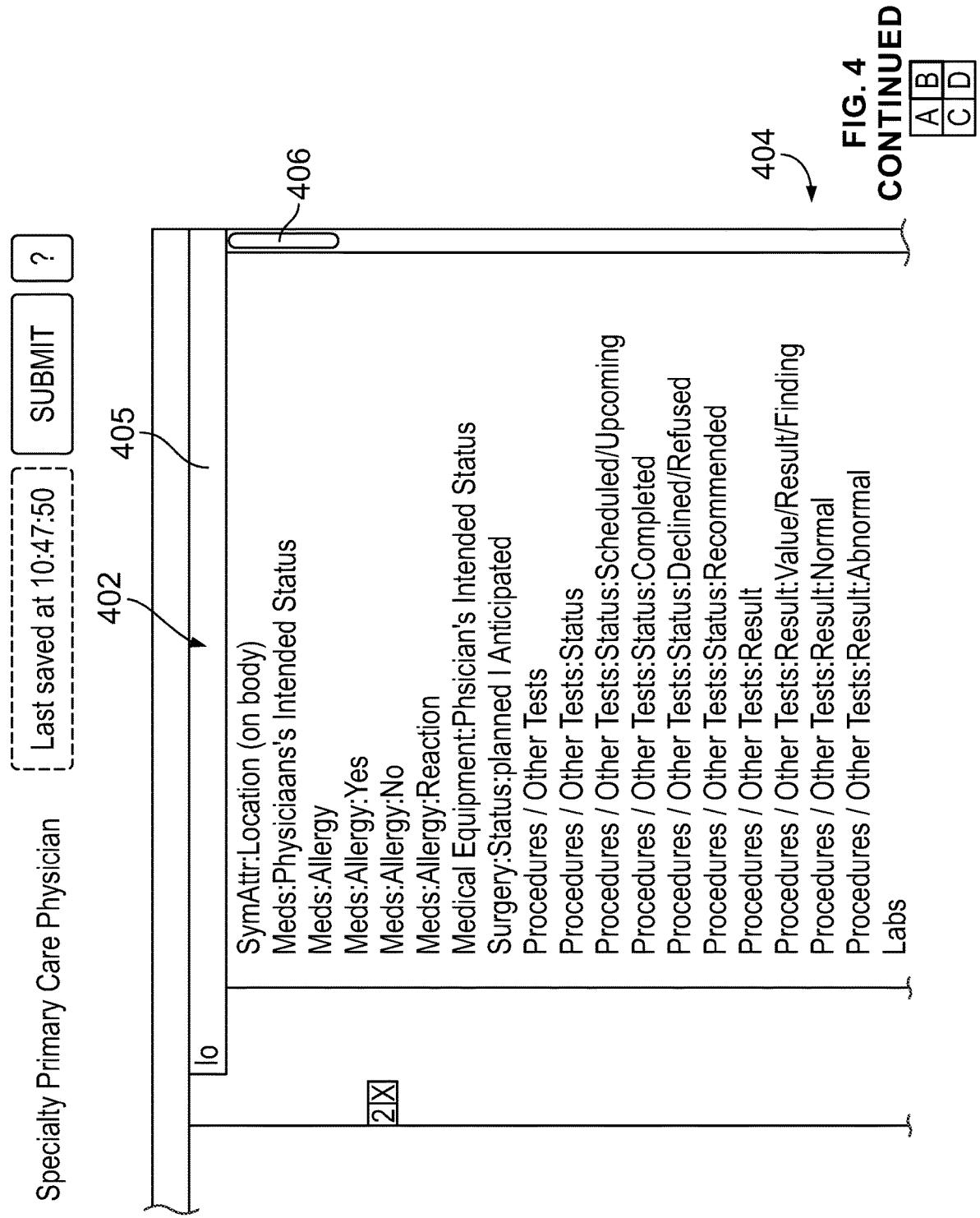
FIG. 4 is an illustration of a transcript of a medical encounter in which the scribe labeler is annotating certain words or phrases in the text.
Figure 4:
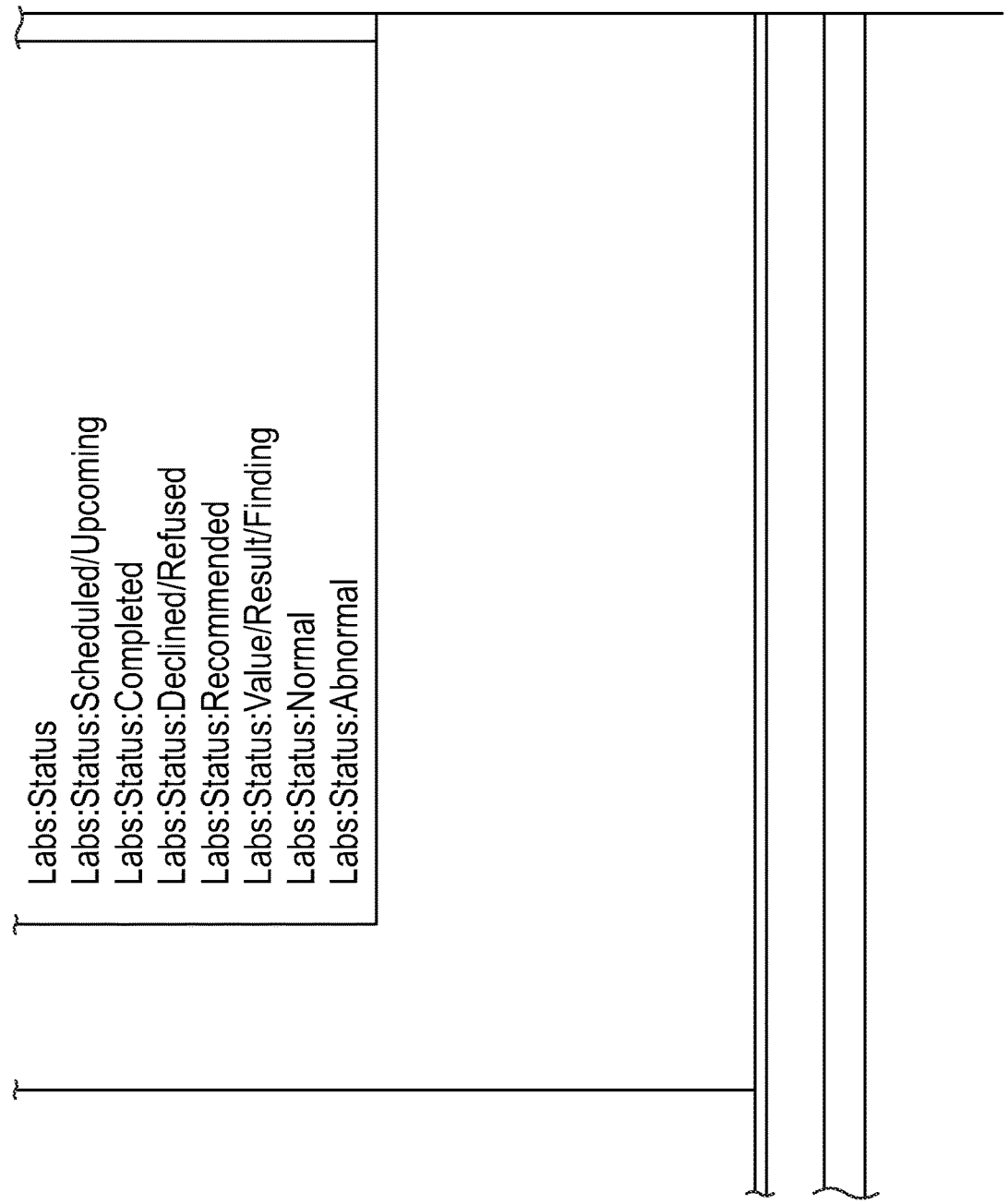

FIG. 4 is an illustration of the display 218 of the user interface along with a transcript 222, and time index 220. Time segment information for each utterance (sentence or word) is provided in the transcript and the time index 220 provides a slider tool 221 which moves right and left to jump to different portions of the transcript.

The interface provides a tool for text highlighting. In particular, mouse and keyboard shortcuts make highlighting spans of text easy. For example, a user can double click on a given word and the word is automatically highlighted on the display. Only words can be highlighted, not individual characters, reducing errors and increasing annotation speed. Other tools could be used for highlighting, such as by click and drag techniques with a mouse, a keyboard stroke (such as by putting the cursor over the word and hitting a particular key such as H, or CTRL-H), or a combination keyboard stroke and mouse action.

In the example of FIG. 4, the user has highlighted the word "stomachache" (see 400). The user interface provides a tool for text tagging, i.e., labelling the highlighted term. Labels are applied to the highlighted spans of text essentially allowing the scribe labeler to inject information into the transcript, for example to indicate that the highlighted text "stomachache" is a symptom, or a gastrointestinal symptom. In particular, when the user has highlighted the term "stomachache", a box (tool) 402 pops up which shows a list 404 of medical entities and associate attributes, a search term entry field 405 by which they can search the list 404, and a scroll bar 406 allowing the scribe labeler to scroll through the list and select a medical entity and associate attribute which is appropriate for the highlighted test. In the example FIG. 4, the medical entity "Symptom:GI" and associated attribute "abdominal pain" was found in the list 404 and the user clicked on that combination of medical entity and attribute. The display includes a Table tab 410 at the bottom of the display which lists the labelled spans of text, including medical entity, attribute, location in the transcript (line 4) and the associated text span ("stomachache").

The scribe labeler does the same process and uses the same tools to highlight the span of text "three days", assign a label of medical entity "SymAttr" and attribute "duration" ("Symattr/duration") to the highlighted span of text "three days" and this additional annotation shows up in the Table of annotations 410.

Figure 5:
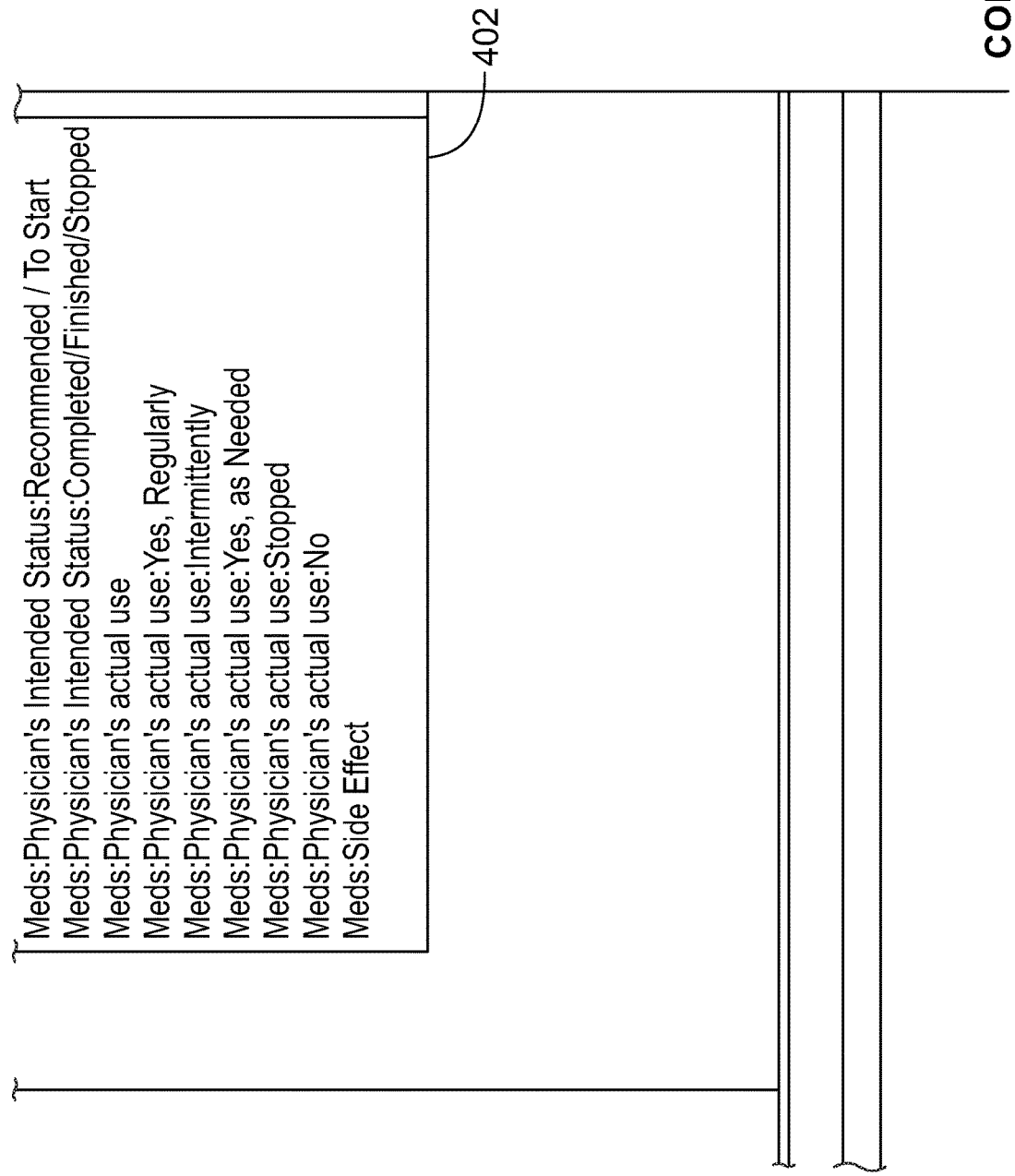
FIG. 5 is an illustration of the transcript of FIG. 4 in which the scribe labeler is annotating the text "upper left" and a search box which pops up. Additionally, a proposed label for the phrase "upper left" for the medical entity "symptom" and attribute "location (on body)" is also displayed. The proposed label is generated by a pre-labelling system shown in FIG. 1.

The scribe labeler then proceeds to highlight the span of text "upper left", 412. The scribe labeler again uses the tool 402 to ascribe a label to the span of text "upper left." Again this could be done using the tools described in FIG. 4. As shown in FIG. 5, in one embodiment where there is pre-labelling of the transcript, when the user highlights the span of text "upper left" a suggested label is shown in the box 502. This suggested label was assigned to the span of text "upper left" by the pre-labeler of FIG. 1. The user can accept this suggestion by clicking on the box 502, or reject the suggestion by clicking on the X icon 504. In the situation of FIG. 5 the scribe labeler accepted the suggestion by a mouse click (or any other alternative suitable user interface action, such as keyboard shortcut etc.) and the annotation is added to the Table 410 as shown in FIG. 5 at 506. If the scribe labeler rejects the suggestion they can use the pop-up search tool 402 or scroll through the list of labels to find a suitable label.

It will be appreciated that the search tool 402 could pop up when the scribe labeler is taking action to highlight a span of text, and disappear after the label has been assigned, or alternatively it could be a persistent feature of the user interface during annotating.

As noted previously, the user interface of FIGS. 2 and 4-6 includes a tool for permitting the scribe labeler to group together highlighted and labelled spans of text which are conceptually or causally related to each other. For example, in FIG. 6 the spans of text "stomachache", and "three days" are related to a gastrointestinal symptom, namely the type of symptom and the duration of the symptom. To make this grouping, the interface provides a tool in the form of combination of key strokes and mouse actions in the illustrated embodiment. In particular, the scribe labeler holds down the "G" key, clicks on the two highlighted spans of text, and then releases the "G" key. Of course, variations from this specific example of the tool for forming a grouping are possible and within the scope of this disclosure, such as combinations of mouse actions alone (e.g., selecting spans of text with a left click and then a right click to form the group), key strokes alone (e.g., ALT-G to select the highlighted spans of text and then ENTER to form the group), or other various possible combinations of mouse actions and key strokes. In FIG. 6, the "2" icon 602 indicates the number of elements in the grouping (here two). The "X" icon 604 is click target to delete the grouping. The user has toggled the Groups tab 606 and the group of "stomachache" and "three-days" is shown as indicated at 608, along with the location in the transcript (line 4 for the location first element in the group in this example).

The search tool 402 of FIG. 4 makes the process of locating the relevant label easy to navigate. In the example of medical transcripts, there may many hundreds of possible labels to choose from. For example, there may be ten or twenty predefined different medical entities and ten or twenty or more different attributes for each of the medical entities. The medical entities may be customized and organized in a hierarchical manner, as explained previously. These labels encode a medical ontology that is designed specifically for medical documentation. These labels encode medical entity information, such as medication, procedures, symptoms, conditions, etc., as well as attributes of the entities, such as onset, severity, frequency, etc., of a symptom, and whether or not the patient declined or refused (attributes) a medical procedure (entity).

The text grouping as shown in FIG. 6 allows the scribe labeler to inject additional information into the transcript and in particular identify relationships or relatedness between concepts. For example the system and method of this disclosure allows the scribe labelers to specify groups of highlighted text such that entities can be associated with the attributes as a group.

The pre-labelling system 110 of FIG. 1 is shown in more detail in FIG. 7. The input to the system 110 is a text transcript 702 generated at step 108 of FIG. 1. The system 110 uses a machine learning medical named entity recognition (NER) model 703 which identifies candidate information (words or phrases) in the transcript and suggested labels for such words or phrases based on supervised learning from trained examples, in the form of a pre-annotated transcript 704. Named entity recognition models are well known in the field of machine learning and are described extensively in the scientific literature. The NER model 703 needs its owned labelled training data. For this training data we use a large corpus of medical text books (over 120,000 medical text books) using deep learning word embedding, in conjunction with a large lexicon of existing medical ontologies, e.g., UMLS (unified medical language system) and SNOMED (systemized nomenclature of medicine). Additionally, the NER can be trained from annotated medical encounter transcripts. A NER model can also be trained from a hybrid of data sources, which may include medical and clinical text books, annotated transcripts from doctor-patient conversations, and clinical documentation contained in anonymized electronic health records of a multitude of patients. The NER model may further be trained from feedback of the annotation of the transcript as performed in FIG. 1 and FIG. 7. For example, after the pre-labeling system generates the pre-annotated transcript 704 and the scribe labeler has proceeded to complete the annotation at step 108, there can be feedback of corrections between the suggested annotations in pre-annotated transcript 704 and annotated transcript 112 back into the NER model.

Figure 8:
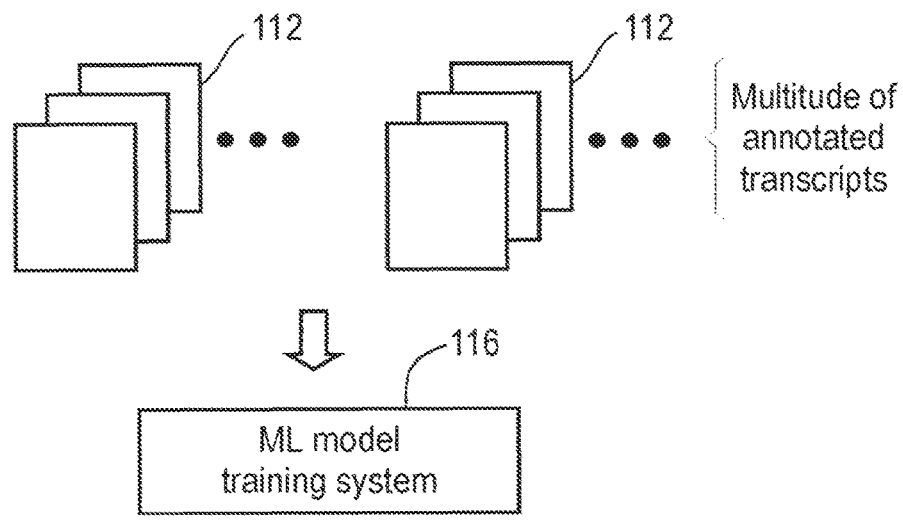
FIG. 8 is an illustration of a machine learning model training system which receives as input a multitude of annotated transcripts in accordance with the features of FIG. 1.

As shown in FIG. 8, the annotated transcripts 112 can be supplied to a machine learning model training system. In one form, the model training system 116 uses the transcripts, along with other patient data, from a multitude of patients to generate machine learning models to make health predictions. Alternatively, the annotated transcripts could be used in the system 116 to develop deep learning models for automating the process of generating annotated transcripts of medical encounters.

The system and method of this disclosure has several advantages. In many natural language processing text annotation tools, relationships between must be identified in an explicit and cumbersome manner. In contrast, in this disclosure the labels (including predefined labels relevant to the annotation task) and labelling and groupings tools permit such relationships to be readily specified. The user can quickly search for labels by means of the search tools as shown in the Figures and select them with simple user interface action such as a click of a mouse. Moreover, groupings of conceptually or causally related highlighted spans of text can be created very quickly with simple user interface actions using a keyboard, mouse, or combination thereof, as explained above.

While the illustrated embodiment has described an interface and tools for assisting in labeling transcripts of medical encounters, the principles of this disclosure could be applied to other situations. In particular, a predefined list of labels is generated for entities and attributes of those entities, e.g., listing all the possible categories or classes of words of interest in a transcript and attributes associated with each of the categories or classes, analogous to the attributes of medical entities. The user interface actions described above would generally be performed in the same way, that is the scribe labeler would read the transcript and highlight words or other spans of text that are relevant to the annotation task, using simple user interface tools, and then tools would be enabled by which the scribe labeler could search through the available labels and assign them to the highlighted spans of text. Additionally, grouping tools are provided to form groups of related highlighted spans of text. The result is an annotated transcript. The methods could have usefulness in other types of transcripts, such as deposition or trial transcripts in the context of the legal profession, hearing transcripts of testimony of governmental bodies, etc.

An example of a list of labels for use in annotation of medical transcripts is set forth below in Table 1. It will be understood of course that variation from the list is possible and that in other contexts other labels will be defined. In the list, Entity 1 is a medical entity and Entity 2 is either a subcategory of the medical entity of Entity 1 or an attribute of the medical entity, and Entity 3 is either an attribute of the medical entity or a further subcategory of the medical entity of Entity 1 in a hierarchical schema.

TABLE 1

| Entity 1 | Entity 2 | Entity 3 | Combined Label that will show up in labeling tool |
|---|---|---|---|
| NOS | | | NOS: |
| SymAttr | Time of Onset | | SymAttr: Time of Onset |
| SymAttr | Frequency/Tempo | | SymAttr: Frequency/Tempo |
| SymAttr | Duration | | SymAttr: Duration |
| SymAttr | Improving/Worsening | | SymAttr: Improving/Worsening |
| SymAttr | Location (on body) | | SymAttr: Location (on body) |
| SymAttr | Severity/Amount | | SymAttr: Severity/Amount |
| SymAttr | Characteristic/Quality | | SymAttr: Characteristic/Quality |
| SymAttr | Provoking Factor | | SymAttr: Provoking Factor |
| SymAttr | Alleviating Factor | | SymAttr: Alleviating Factor |
| SymAttr | Radiation | | SymAttr: Radiation |
| SymAttr | Not Experienced | | SymAttr: Not Experienced |
| SymAttr | | | SymAttr: |
| Chief Complaint | | | Chief Complaint:: |
| Meds | | | Meds:: |
| Meds | Physician's Intended Status | | Meds: Physician's Intended Status: |
| Meds | Physician's Intended Status | Active, Continued | Meds: Physician's Intended Status: Active, Continued |
| Meds | Physician's Intended Status | Active, Modified | Meds: Physician's Intended Status: Active, Modified |
| Meds | Physician's Intended Status | Recommended/To Start | Meds: Physician's Intended Status: Recommended/To Start |
| Meds | Physician's Intended Status | Completed/Finished/ Stopped | Meds: Physician's Intended Status: Completed/Finished/ Stopped |
| Meds | Patient's actual use | | Meds: Patient's actual use: |
| Meds | Patient's actual use | Yes, Regularly | Meds: Patient's actual use: Yes, Regularly |
| Meds | Patient's actual use | Yes, Intermittently | Meds: Patient's actual use: Yes, Intermittently |
| Meds | Patient's actual use | Yes, as Needed | Meds: Patient's actual use: Yes, as Needed |
| Meds | Patient's actual use | Stopped | Meds: Patient's actual use: Stopped |
| Meds | Patient's actual use | No | Meds: Patient's actual use: No |
| Meds | Side Effect | | Meds: Side Effect: |
| Meds | Side Effect | Experienced | Meds: Side Effect: Experienced |
| Meds | Side Effect | No | Meds: Side Effect: No |
| Meds | Benefit | | Meds: Benefit: |
| Meds | Benefit | Experienced | Meds: Benefit: Experienced |
| Meds | Benefit | No | Meds: Benefit: No |
| Meds | Dosage | | Meds: Dosage: |
| Meds | Quantity | | Meds: Quantity: |
| Meds | Frequency/Duration | | Meds: Frequency/Duration: |
| Meds | Instructions/Directions | | Meds: Instructions/Directions: |
| Meds | Route of Administration | | Meds: Route of Administration: |
| Meds | Indication | | Meds: Indication: |
| Meds | Allergy | | Meds: Allergy: |
| Meds | Allergy | Yes | Meds: Allergy: Yes |
| Meds | Allergy | No | Meds: Allergy: No |
| Meds | Allergy | Reaction | Meds: Allergy: Reaction |
| Medical Equipment | | | Medical Equipment:: |
| Medical Equipment | Physician's Intended Status | | Medical Equipment: Physician's Intended Status: |
| Medical Equipment | Physician's Intended Status | Active, Continued | Medical Equipment: Physician's Intended Status: Active, Continued |
| Medical Equipment | Physician's Intended Status | Active, Modified | Medical Equipment: Physician's Intended Status: Active, Modified |
| Medical Equipment | Physician's Intended Status | Recommended/To Start | Medical Equipment: Physician's Intended Status: Recommended/To Start |

TABLE 1-continued

| Entity 1 | Entity 2 | Entity 3 | Combined Label that will show up in labeling tool |
|---|---|---|---|
| Medical Equipment | Physician's Intended Status | Completed/Finished/Stopped | Medical Equipment: Physician's Intended Status: Completed/Finished/Stopped |
| Medical Equipment | Patient's actual use | | Medical Equipment: Patient's actual use: |
| Medical Equipment | Patient's actual use | Yes, Regularly | Medical Equipment: Patient's actual use: Yes, Regularly |
| Medical Equipment | Patient's actual use | Yes, Intermittently | Medical Equipment: Patient's actual use: Yes, Intermittently |
| Medical Equipment | Patient's actual use | Yes, as Needed | Medical Equipment: Patient's actual use: Yes, as Needed |
| Medical Equipment | Patient's actual use | Stopped | Medical Equipment: Patient's actual use: Stopped |
| Medical Equipment | Patient's actual use | No | Medical Equipment: Patient's actual use: No |
| Medical Equipment | Side Effect | | Medical Equipment: Side Effect: |
| Medical Equipment | Side Effect | Experienced | Medical Equipment: Side Effect: Experienced |
| Medical Equipment | Side Effect | No | Medical Equipment: Side Effect: No |
| Medical Equipment | Benefit | | Medical Equipment: Benefit: |
| Medical Equipment | Benefit | Experienced | Medical Equipment: Benefit: Experienced |
| Medical Equipment | Benefit | No | Medical Equipment: Benefit: No |
| Medical Equipment | Dosage | | Medical Equipment: Dosage: |
| Medical Equipment | Quantity | | Medical Equipment: Quantity: |
| Medical Equipment | Frequency/Duration | | Medical Equipment: Frequency/Duration: |
| Medical Equipment | Instructions/Directions | | Medical Equipment: Instructions/Directions: |
| Medical Equipment | Indication | | Medical Equipment: Indication: |
| Condition | | | Condition:: |
| Condition | Status | | Condition: Status: |
| Condition | Status | Active | Condition: Status: Active |
| Condition | Status | Recurrence | Condition: Status: Recurrence |
| Condition | Status | Inactive | Condition: Status: Inactive |
| Condition | Status | Remission | Condition: Status: Remission |
| Condition | Status | Resolved | Condition: Status: Resolved |
| Condition | Time of Onset/Duration | | Condition: Time of Onset/Duration: |
| Condition | Physician certainty | | Condition: Physician certainty: |
| Condition | Physician certainty | Provisional/Differential | Condition: Physician certainty: Provisional/Differential |
| Condition | Physician certainty | Confirmed | Condition: Physician certainty: Confirmed |
| Condition | Physician certainty | Refuted | Condition: Physician certainty: Refuted |
| Condition | Severity | New | Condition: Severity: New |
| Condition | Severity | Stable | Condition: Severity: Stable |
| Condition | Severity | Improved | Condition: Severity: Improved |
| Condition | Severity | Worsening | Condition: Severity: Worsening |
| Condition | Family | | Condition: Family: |
| Condition | Family | History of (First Degree) | Condition: Family: History of (First Degree) |
| Condition | Family | History of (Non-first-degree) | Condition: Family: History of (Non-first-degree) |
| Surgery | | | Surgery:: |
| Surgery | Status | | Surgery: Status: |
| Surgery | Status | Completed | Surgery: Status: Completed |
| Surgery | Status | Planned/Anticipated | Surgery: Status: Planned/Anticipated |
| Procedures/Other Tests | | | Procedures/Other Tests:: |
| Procedures/Other Tests | Status | | Procedures/Other Tests: Status: |
| Procedures/Other Tests | Status | Scheduled/Upcoming | Procedures/Other Tests: Status: Scheduled/Upcoming |
| Procedures/Other Tests | Status | Completed | Procedures/Other Tests: Status: Completed |

TABLE 1-continued

| Entity 1 | Entity 2 | Entity 3 | Combined Label that will show up in labeling tool |
|---|---|---|---|
| Procedures/Other Tests | Status | Not done | Procedures/Other Tests: Status: Not done |
| Procedures/Other Tests | Status | Declined/Refused | Procedures/Other Tests: Status: Declined/Refused |
| Procedures/Other Tests | Status | Recommended | Procedures/Other Tests: Status: Recommended |
| Procedures/Other Tests | Result | | Procedures/Other Tests: Result: |
| Procedures/Other Tests | Result | Value/Result/Finding | Procedures/Other Tests: Result: Value/Result/Finding |
| Procedures/Other Tests | Result | Normal | Procedures/Other Tests: Result: Normal |
| Procedures/Other Tests | Result | Abnormal | Procedures/Other Tests: Result: Abnormal |
| Labs | | | Labs:: |
| Labs | Status | | Labs: Status: |
| Labs | Status | Scheduled/Upcoming | Labs: Status: Scheduled/Upcoming |
| Labs | Status | Completed | Labs: Status: Completed |
| Labs | Status | Declined/Refused | Labs: Status: Declined/Refused |
| Labs | Status | Recommended | Labs: Status: Recommended |
| Labs | Result | Value/Result/Finding | Labs: Result: Value/Result/Finding |
| Labs | Result | Normal | Labs: Result: Normal |
| Labs | Result | Abnormal | Labs: Result: Abnormal |
| Imaging | | | Imaging:: |
| Imaging | Status | | Imaging: Status: |
| Imaging | Status | Scheduled/Upcoming | Imaging: Status: Scheduled/Upcoming |
| Imaging | Status | Completed | Imaging: Status: Completed |
| Imaging | Status | Declined/Refused | Imaging: Status: Declined/Refused |
| Imaging | Status | Recommended | Imaging: Status: Recommended |
| Imaging | Result | Value/Result/Finding | Imaging: Result: Value/Result/Finding |
| Imaging | Result | Normal | Imaging: Result: Normal |
| Imaging | Result | Abnormal | Imaging: Result: Abnormal |
| Vaccine | | | Vaccine:: |
| Vaccine | Status | | Vaccine: Status: |
| Vaccine | Status | Scheduled/Upcoming | Vaccine: Status: Scheduled/Upcoming |
| Vaccine | Status | Completed | Vaccine: Status: Completed |
| Vaccine | Status | Declined/Refused | Vaccine: Status: Declined/Refused |
| Vaccine | Status | Recommended | Vaccine: Status: Recommended |
| Provider | | | Provider:: |
| Provider | Type | | Provider: Type: |
| Provider | Type | Physician/Practitioner | Provider: Type: Physician/Practitioner |
| Provider | Type | Other Health Professional | Provider: Type: Other Health Professional |
| Provider | Status of Referral | | Provider: Status of Referral: |
| Provider | Status of Referral | Recommended/To Start | Provider: Status of Referral: Recommended/To Start |
| Provider | Status of Referral | On-going | Provider: Status of Referral On-going |
| Provider | Status of Referral | Discontinued/Stopped | Provider: Status of Referral: Discontinued/Stopped |
| Provider | Status of Referral | Requested | Provider: Status of Referral: Requested |
| Provider | Urgent/Emergency Care | | Provider: Urgent/Emergency Care: |
| Provider | Hospital | | Provider: Hospital: |
| Provider | Follow-up Visit | | Provider: Follow-up Visit: |
| Patient instructions/education/ recommendation | | | Patient instructions/education/ recommendation:: |
| Social Hx | | | Social Hx:: |
| Social Hx | Lifestyle/Wellness Habits | | Social Hx: Lifestyle/Wellness Habits: |
| Social Hx | Tobacco | | Social Hx: Tobacco: |
| Social Hx | Tobacco | Active | Social Hx: Tobacco: Active |
| Social Hx | Tobacco | Second Hand Smoking | Social Hx: Tobacco: Second Hand Smoking |
| Social Hx | Tobacco | Former | Social Hx: Tobacco: Former |
| Social Hx | Tobacco | Never | Social Hx: Tobacco: Never |
| Social Hx | Tobacco | Current Quantity/Freq | Social Hx: Tobacco: Current Quantity/Freq |

TABLE 1-continued

| Entity 1 | Entity 2 | Entity 3 | Combined Label that will show up in labeling tool |
|---|---|---|---|
| Social Hx | Tobacco | Former Quantity/Freq | Social Hx: Tobacco: Former Quantity/Freq |
| Social Hx | Tobacco | Counseling | Social Hx: Tobacco: Counseling |
| Social Hx | Alcohol | | Social Hx: Alcohol: |
| Social Hx | Alcohol | Active | Social Hx: Alcohol: Active |
| Social Hx | Alcohol | Denies | Social Hx: Alcohol: Denies |
| Social Hx | Alcohol | Former | Social Hx: Alcohol: Former |
| Social Hx | Alcohol | Never | Social Hx: Alcohol: Never |
| Social Hx | Alcohol | Current Quantity/Freq | Social Hx: Alcohol: Current Quantity/Freq |
| Social Hx | Alcohol | Former Quantity/Freq | Social Hx: Alcohol: Former Quantity/Freq |
| Social Hx | Alcohol | Counseling | Social Hx: Alcohol: Counseling |
| Social Hx | Marijuana or Drug Use | | Social Hx: Marijuana or Drug Use: |
| Social Hx | Marijuana or Drug Use | Active | Social Hx: Marijuana or Drug Use: Active |
| Social Hx | Marijuana or Drug Use | Former | Social Hx: Marijuana or Drug Use: Former |
| Social Hx | Marijuana or Drug Use | Never | Social Hx: Marijuana or Drug Use: Never |
| Social Hx | Marijuana or Drug Use | Current Quantity/Freq | Social Hx: Marijuana or Drug Use: Current Quantity/Freq |
| Social Hx | Marijuana or Drug Use | Former Quantity | Social Hx: Marijuana or Drug Use: Former Quantity |
| Social Hx | Marijuana or Drug Use | Counseling | Social Hx: Marijuana or Drug Use: Counseling |
| Social Hx | Socio Economic Status | | Social Hx: Socio Economic Status: |
| Social Hx | Socio Economic Status | Home | Social Hx: Socio Economic Status: Home |
| Social Hx | Socio Economic Status | Occupation | Social Hx: Socio Economic Status: Occupation |
| Social Hx | Socio Economic Status | Insurance | Social Hx: Socio Economic Status: Insurance |
| Social Hx | Logistics | | Social Hx: Logistics: |
| Social Hx | Logistics | Transportation | Social Hx: Logistics: Transportation |
| Social Hx | Sexual History | | Social Hx: Sexual History: |
| Social Hx | Sexual History | Active | Social Hx: Sexual History: Active |
| Social Hx | Sexual History | Inactive | Social Hx: Sexual History: Inactive |
| Social Hx | Sexual History | Never | Social Hx: Sexual History: Never |
| Social Hx | Sexual History | Quantity of Partners | Social Hx: Sexual History: Quantity of Partners |
| Social Hx | Travel History | | Social Hx: Travel History: |
| Code Status/ End of Life | Code Status/End of Life | | Code Status/End of Life: Code Status/End of Life: |
| Reproductive Hx | | | Reproductive Hx:: |
| Reproductive Hx | Gravida (Number of Pregnancies) | | Reproductive Hx: Gravida (Number of Pregnancies): |
| Reproductive Hx | Parity (Number of Births Carried to a Viable Gestational Age) | | Reproductive Hx: Parity (Number of Births Carried to a Viable Gestational Age): |
| Reproductive Hx | Number of Premature Births | | Reproductive Hx: Number of Premature Births: |
| Reproductive Hx | Number of Natural Abortions/Miscarriages | | Reproductive Hx: Number of Natural Abortions/Miscarriages: |
| Reproductive Hx | Number of Living Children | | Reproductive Hx: Number of Living Children: |
| Reproductive Hx | Currently Pregnant | | Reproductive Hx: Currently Pregnant: |
| Reproductive Hx | Current Gestational Age | | Reproductive Hx: Current Gestational Age: |
| Reproductive Hx | Anticipating Planned or Unplanned Pregnancy | | Reproductive Hx: Anticipating Planned or Unplanned Pregnancy: |
| Reproductive Hx | Infertility Issue | | Reproductive Hx: Infertility Issue: |
| Reproductive Hx | IVF | | Reproductive Hx: IVF: |
| Reproductive Hx | Last Menstrual Period | | Reproductive Hx: Last Menstrual Period: |

TABLE 1-continued

| Entity 1 | Entity 2 | Entity 3 | Combined Label that will show up in labeling tool |
|---|---|---|---|
| Reproductive Hx | Menarche (Time of First Period) | | Reproductive Hx: Menarche (Time of First Period): |
| Vitals | Ht | | Vitals: Ht: |
| Vitals | Ht | Value/Result/Finding | Vitals: Ht: Value/Result/Finding |
| Vitals | Ht | Normal | Vitals: Ht: Normal |
| Vitals | Ht | Abnormal | Vitals: Ht: Abnormal |
| Vitals | Wt | | Vitals: Wt: |
| Vitals | Wt | Value/Result/Finding | Vitals: Wt: Value/Result/Finding |
| Vitals | Wt | Normal | Vitals: Wt: Normal |
| Vitals | Wt | Abnormal | Vitals: Wt: Abnormal |
| Vitals | BMI | | Vitals: BMI: |
| Vitals | BMI | Value/Result/Finding | Vitals: BMI :Value/Result/Finding |
| Vitals | BMI | Normal | Vitals: BMI: Normal |
| Vitals | BMI | Abnormal | Vitals: BMI: Abnormal |
| Vitals | Temp | | Vitals: Temp: |
| Vitals | Temp | Value/Result/Finding | Vitals: Temp: Value/Result/Finding |
| Vitals | Temp | Normal | Vitals: Temp: Normal |
| Vitals | Temp | Abnormal | Vitals: Temp: Abnormal |
| Vitals | HR | | Vitals: HR: |
| Vitals | HR | Value/Result/Finding | Vitals: HR: Value/Result/Finding |
| Vitals | HR | Normal | Vitals: HR: Normal |
| Vitals | HR | Abnormal | Vitals: HR: Abnormal |
| Vitals | BP | | Vitals: BP: |
| Vitals | BP | Value/Result/Finding | Vitals: BP: Value/Result/Finding |
| Vitals | BP | Normal | Vitals: BP: Normal |
| Vitals | BP | Abnormal | Vitals: BP: Abnormal |
| Vitals | Resp Rate | | Vitals: Resp Rate: |
| Vitals | Resp Rate | Value/Result/Finding | Vitals: Resp Rate: Value/Result/Finding |
| Vitals | Resp Rate | Normal | Vitals: Resp Rate: Normal |
| Vitals | Resp Rate | Abnormal | Vitals: Resp Rate: Abnormal |
| Vitals | O2 | | Vitals: O2: |
| Vitals | O2 | Value/Result/Finding | Vitals: O2: Value/Result/Finding |
| Vitals | O2 | Normal | Vitals: O2: Normal |
| Vitals | O2 | Abnormal | Vitals: O2: Abnormal |
| Exam | General | | Exam: General: |
| Exam | General | Value/Result/Finding | Exam: General: Value/Result/Finding |
| Exam | Const | | Exam: Const: |
| Exam | Const | Value/Result/Finding | Exam: Const: Value/Result/Finding |
| Exam | Eyes | | Exam: Eyes: |
| Exam | Eyes | Value/Result/Finding | Exam: Eyes: Value/Result/Finding |
| Exam | ENMT | | Exam: ENMT: |
| Exam | ENMT | Value/Result/Finding | Exam: ENMT : Value/Result/Finding |
| Exam | Dental | | Exam: Dental: |
| Exam | Dental | Value/Result/Finding | Exam: Dental: Value/Result/Finding |
| Exam | Neck | | Exam: Neck: |
| Exam | Neck | Value/Result/Finding | Exam: Neck: Value/Result/Finding |
| Exam | Resp/Pulm | | Exam: Resp/Pulm: |
| Exam | Resp/Pulm | Value/Result/Finding | Exam: Resp/Pulm: Value/Result/Finding |
| Exam | CV | | Exam: CV: |
| Exam | CV | Value/Result/Finding | Exam: CV: Value/Result/Finding |
| Exam | Lymph | | Exam: Lymph: |
| Exam | Lymph | Value/Result/Finding | Exam: Lymph: Value/Result/Finding |
| Exam | GU | | Exam: GU: |
| Exam | GU | Value/Result/Finding | Exam: GU: Value/Result/Finding |
| Exam | MSK | | Exam: MSK: |
| Exam | MSK | Value/Result/Finding | Exam: MSK: Value/Result/Finding |
| Exam | Derm | | Exam: Derm: |
| Exam | Derm | Value/Result/Finding | Exam: Derm: Value/Result/Finding |
| Exam | Neuro | | Exam: Neuro: |
| Exam | Neuro | Value/Result/Finding | Exam: Neuro: Value/Result/Finding |
| Exam | Abd | | Exam: Abd: |
| Exam | Abd | Value/Result/Finding | Exam: Abd: Value/Result/Finding |
| Exam | Breast | | Exam: Breast: |
| Exam | Breast | Value/Result/Finding | Exam: Breast: Value/Result/Finding |
| Exam | Rectal | | Exam: Rectal: |
| Exam | Rectal | Value/Result/Finding | Exam: Rectal: Value/Result/Finding |
| Exam | Prostate | | Exam: Prostate: |
| Exam | Prostate | Value/Result/Finding | Exam: Prostate: Value/Result/Finding |
| Exam | Hernia | | Exam: Hernia: |
| Exam | Hernia | Value/Result/Finding | Exam: Hernia: Value/Result/Finding |
| Exam | Bimanual/GYN | | Exam: Bimanual/GYN: |
| Exam | Bimanual/GYN | Value/Result/Finding | Exam: Bimanual/GYN: Value/Result/Finding |

TABLE 1-continued

| Entity 1 | Entity 2 | Entity 3 | Combined Label that will show up in labeling tool |
|---|---|---|---|
| Exam | Psych | | Exam: Psych: |
| Exam | Psych | Value/Result/Finding | Exam: Psych: Value/Result/Finding |
| Exam | Extremities | | Exam: Extremities: |
| Exam | Extremities | Value/Result/Finding | Exam: Extremities: Value/Result/Finding |
| Sym | Const | | Sym: Const:: |
| Sym | Const | Fever | Sym: Const: Fever: |
| Sym | Const | Chills | Sym: Const: Chills: |
| Sym | Const | Night Sweats | Sym: Const: Night Sweats: |
| Sym | Const | Body Aches | Sym: Const: Body Aches: |
| Sym | Const | Pain (Non-specific) | Sym: Const: Pain (Non-specific): |
| Sym | Const | Fatigue | Sym: Const: Fatigue: |
| Sym | Const | Lightheadedness | Sym: Const: Lightheadedness: |
| Sym | Const | Difficulty Sleeping | Sym: Const: Difficulty Sleeping: |
| Sym | Const | General Weakness | Sym: Const: General Weakness: |
| Sym | Const | Weight Loss | Sym: Const: Weight Loss: |
| Sym | Const | Weight Gain | Sym: Const: Weight Gain: |
| Sym | Eyes | | Sym: Eyes:: |
| Sym | Eyes | Change in Vision | Sym: Eyes: Change in Vision: |
| Sym | Eyes | Double Vision (Diplopia) | Sym: Eyes: Double Vision (Diplopia): |
| Sym | Eyes | Flashers (Photopsia) | Sym: Eyes: Flashers (Photopsia): |
| Sym | Eyes | Sensitivity to Light (Photophobia) | Sym: Eyes: Sensitivity to Light (Photophobia): |
| Sym | Eyes | Eye Pain | Sym: Eyes: Eye Pain: |
| Sym | Eyes | Eye Discharge | Sym: Eyes: Eye Discharge: |
| Sym | Eyes | Red Eye | Sym: Eyes: Red Eye: |
| Sym | Eyes | Dry Eye | Sym: Eyes: Dry Eye: |
| Sym | ENMT | | Sym: ENMT:: |
| Sym | ENMT | Ear Pain (Otalgia) | Sym: ENMT: Ear Pain (Otalgia): |
| Sym | ENMT | Ear Discharge (Otorrhea) | Sym: ENMT: Ear Discharge (Otorrhea): |
| Sym | ENMT | Swollen Ear | Sym: ENMT: Swollen Ear: |
| Sym | ENMT | Hearing Loss | Sym: ENMT: Hearing Loss: |
| Sym | ENMT | Sensitivity to Sounds (Phonophobia or Hyperacusis) | Sym: ENMT: Sensitivity to Sounds (Phonophobia or Hyperacusis): |
| Sym | ENMT | Ear Ringing (Tinnitus) | Sym: ENMT: Ear Ringing (Tinnitus): |
| Sym | ENMT | Nose Bleeding (Epistaxis) | Sym: ENMT: Nose Bleeding (Epistaxis): |
| Sym | ENMT | Nasal Discharge (Rhinorrhea) | Sym: ENMT: Nasal Discharge (Rhinorrhea): |
| Sym | ENMT | Nasal Congestion | Sym: ENMT: Nasal Congestion: |
| Sym | ENMT | Loss of Smell | Sym: ENMT: Loss of Smell: |
| Sym | ENMT | Sinus Issue | Sym: ENMT: Sinus Issue: |
| Sym | ENMT | Sore Throat | Sym: ENMT: Sore Throat: |
| Sym | ENMT | Oral Sores/Lesions | Sym: ENMT: Oral Sores/Lesions: |
| Sym | ENMT | Painful Swallowing (Odynophagia) | Sym: ENMT: Painful Swallowing (Odynophagia): |
| Sym | ENMT | Loss of Taste | Sym: ENMT: Loss of Taste: |
| Sym | ENMT | Tooth Pain | Sym: ENMT: Tooth Pain: |
| Sym | ENMT | Bleeding Gums (Gingival Hemorrhage) | Sym: ENMT: Bleeding Gums (Gingival Hemorrhage): |
| Sym | ENMT | Hoarse Voice | Sym: ENMT: Hoarse Voice: |
| Sym | ENMT | Change in Voice | Sym: ENMT: Change in Voice: |
| Sym | ENMT | Neck Pain | Sym: ENMT: Neck Pain: |
| Sym | ENMT | Change of Taste (Dysgeusia) | Sym: ENMT: Change of Taste (Dysgeusia): |
| Sym | CV | | Sym: CV:: |
| Sym | CV | Chest Pain (Angina) | Sym: CV: Chest Pain (Angina): |
| Sym | CV | Palpitations | Sym: CV: Palpitations: |
| Sym | CV | Leg Swelling (Edema) | Sym: CV: Leg Swelling (Edema): |
| Sym | CV | Leg Pain with walking (Claudication) | Sym: CV: Leg Pain with walking (Claudication): |
| Sym | CV | Fainting/Syncope | Sym: CV: Fainting/Syncope: |
| Sym | Resp | | Sym: Resp:: |
| Sym | Resp | Cough | Sym: Resp: Cough: |
| Sym | Resp | Hemoptysis | Sym: Resp: Hemoptysis: |
| Sym | Resp | Wheezing | Sym: Resp: Wheezing: |

TABLE 1-continued

| Entity 1 | Entity 2 | Entity 3 | Combined Label that will show up in labeling tool |
|---|---|---|---|
| Sym | Resp | SOB Lying Flat (Orthopnea) | Sym: Resp: SOB Lying Flat (Orthopnea): |
| Sym | Resp | SOB when Waking up (Paroxysmal Nocturnal Dyspnea) | Sym: Resp: SOB when Waking up (Paroxysmal Nocturnal Dyspnea): |
| Sym | Resp | SOB | Sym: Resp: SOB: |
| Sym | GI | | Sym: GI:: |
| Sym | GI | Decreased Appetite | Sym: GI: Decreased Appetite: |
| Sym | GI | Nausea | Sym: GI: Nausea: |
| Sym | GI | Vomiting | Sym: GI: Vomiting: |
| Sym | GI | Difficulty Swallowing (Dysphagia) | Sym: GI: Difficulty Swallowing (Dysphagia): |
| Sym | GI | Jaundice | Sym: GI: Jaundice: |
| Sym | GI | Abdominal Pain | Sym: GI: Abdominal Pain: |
| Sym | GI | Abdominal Distension | Sym: GI: Abdominal Distension: |
| Sym | GI | Change in Bowel Habits | Sym: GI: Change in Bowel Habits: |
| Sym | GI | Diarrhea | Sym: GI: Diarrhea: |
| Sym | GI | Constipation | Sym: GI: Constipation: |
| Sym | GI | Stool Incontinence (Encopresis) | Sym: GI: Stool Incontinence (Encopresis): |
| Sym | GI | Bright Red Blood Per Rectum (Hematochezia) | Sym: GI: Bright Red Blood Per Rectum (Hematochezia): |
| Sym | GI | Black Tarry Stools (Melena) | Sym: GI: Black Tarry Stools (Melena): |
| Sym | GI | GI Bleeding (Non-specific) | Sym: GI: GI Bleeding (Non-specific): |
| Sym | GI | Anal Pain | Sym: GI: Anal Pain: |
| Sym | GU | | Sym: GU:: |
| Sym | GU | Pelvic Pain | Sym: GU: Pelvic Pain: |
| Sym | GU | Sexually Transmitted Disease Exposure | Sym: GU: Sexually Transmitted Disease Exposure: |
| Sym | GU | Frequent Urination | Sym: GU: Frequent Urination: |
| Sym | GU | Decreased Urination | Sym: GU: Decreased Urination: |
| Sym | GU | Urgent Urination | Sym: GU: Urgent Urination: |
| Sym | GU | Urinary Hesitancy | Sym: GU: Urinary Hesitancy: |
| Sym | GU | Burning with Urination (Dysuria) | Sym: GU: Burning with Urination (Dysuria): |
| Sym | GU | Blood in urine (Hematuria) | Sym: GU: Blood in urine (Hematuria): |
| Sym | GU | Changes in Urine Quality (Non-bloody) | Sym: GU: Changes in Urine Quality (Non-bloody): |
| Sym | GU | Incomplete Bladder Emptying (Urinary Retention) | Sym: GU: Incomplete Bladder Emptying (Urinary Retention): |
| Sym | GU | Urinary Incontinence | Sym: GU: Urinary Incontinence: |
| Sym | GU | Penile Discharge | Sym: GU: Penile Discharge: |
| Sym | GU | Penile Ulcers | Sym: GU: Penile Ulcers: |
| Sym | GU | Testicular Pain | Sym: GU: Testicular Pain: |
| Sym | GU | Scrotal Mass/Swelling | Sym: GU: Scrotal Mass/Swelling: |
| Sym | GU | Difficulty Obt. or Maint. an Erection (Erectile Dysfunction) | Sym: GU: Difficulty Obt. or Maint. an Erection (Erectile Dysfunction): |
| Sym | GU | Heavy Menstrual Bleeding (Menorrhagia) | Sym: GU: Heavy Menstrual Bleeding (Menorrhagia): |
| Sym | GU | Menstrual Regularity | Sym: GU: Menstrual Regularity: |
| Sym | GU | Irregular Menstrual Bleeding (Metrorrhagia) | Sym: GU: Irregular Menstrual Bleeding (Metrorrhagia): |
| Sym | GU | Vaginal Bleeding after Menopause | Sym: GU: Vaginal Bleeding after Menopause: |
| Sym | GU | Menstrual Pain (dysmenorrhea) | Sym: GU: Menstrual Pain (dysmenorrhea): |
| Sym | GU | Vaginal Discharge | Sym: GU: Vaginal Discharge: |
| Sym | GU | Vaginal/Vulva ulcers | Sym: GU: Vaginal/Vulva ulcers: |
| Sym | GU | Pain with Sexual Intercourse (Dyspareunia) | Sym: GU: Pain with Sexual Intercourse (Dyspareunia): |

TABLE 1-continued

| Entity 1 | Entity 2 | Entity 3 | Combined Label that will show up in labeling tool |
|---|---|---|---|
| Sym | GU | Vaginal Dryness | Sym: GU: Vaginal Dryness: |
| Sym | MSK | | Sym: MSK:: |
| Sym | MSK | Pain | Sym: MSK: Pain: |
| Sym | MSK | Swelling | Sym: MSK: Swelling: |
| Sym | MSK | Decreased Range Of Motion | Sym: MSK: Decreased Range Of Motion: |
| Sym | Skin/Br | | Sym: Skin/Br:: |
| Sym | Skin/Br | Rash | Sym: Skin/Br: Rash: |
| Sym | Skin/Br | Stria | Sym: Skin/Br: Stria: |
| Sym | Skin/Br | Wounds | Sym: Skin/Br: Wounds: |
| Sym | Skin/Br | Incisions | Sym: Skin/Br: Incisions: |
| Sym | Skin/Br | Scrapes | Sym: Skin/Br: Scrapes: |
| Sym | Skin/Br | Sores/Ulcers | Sym: Skin/Br: Sores/Ulcers: |
| Sym | Skin/Br | Skin Darkening | Sym: Skin/Br: Skin Darkening: |
| Sym | Skin/Br | Hair Loss | Sym: Skin/Br: Hair Loss: |
| Sym | Skin/Br | Thinning Hair | Sym: Skin/Br: Thinning Hair: |
| Sym | Skin/Br | Sun sensitivity | Sym: Skin/Br: Sun sensitivity: |
| Sym | Skin/Br | Skin Itch (Pruritis) | Sym: Skin/Br: Skin Itch (Pruritis): |
| Sym | Skin/Br | Breast Lumps | Sym: Skin/Br: Breast Lumps: |
| Sym | Skin/Br | Breast Pain | Sym: Skin/Br: Breast Pain: |
| Sym | Skin/Br | Nipple Discharge | Sym: Skin/Br: Nipple Discharge: |
| Sym | Skin/Br | Fingers/Toes/Extremities Turn Colors in Cold | Sym: Skin/Br: Fingers/Toes/Extremities Turn Colors in Cold: |
| Sym | Skin/Br | Nail Issue | Sym: Skin/Br: Nail Issue: |
| Sym | Skin/Br | Dry Skin | Sym: Skin/Br: Dry Skin: |
| Sym | Skin/Br | Scalp Tenderness | Sym: Skin/Br: Scalp Tenderness: |
| Sym | Neuro | | Sym: Neuro:: |
| Sym | Neuro | Pain | Sym: Neuro: Pain: |
| Sym | Neuro | Sensation changes (Numbness/Coldness/Crawling/Prickling/Parasthesias) | Sym: Neuro: Sensation changes (Numbness/Coldness/Crawling/Prickling/Parasthesias): |
| Sym | Neuro | Memory Loss | Sym: Neuro: Memory Loss: |
| Sym | Neuro | Difficulty Thinking/Changes in Mentation | Sym: Neuro: Difficulty Thinking/Changes in Mentation: |
| Sym | Neuro | Seizures | Sym: Neuro: Seizures: |
| Sym | Neuro | Tremor | Sym: Neuro: Tremor: |
| Sym | Neuro | Dizziness | Sym: Neuro: Dizziness: |
| Sym | Neuro | Speech Problems | Sym: Neuro: Speech Problems: |
| Sym | Neuro | Non-general Weakness | Sym: Neuro: Non-general Weakness: |
| Sym | Neuro | Muscle Cramps | Sym: Neuro: Muscle Cramps: |
| Sym | Neuro | Jaw Pain with Chewing | Sym: Neuro: Jaw Pain with Chewing: |
| Sym | Neuro | Headache | Sym: Neuro: Headache: |
| Sym | Psych | | Sym: Psych:: |
| Sym | Psych | Anxiety | Sym: Psych: Anxiety: |
| Sym | Psych | Depressed Mood | Sym: Psych: Depressed Mood: |
| Sym | Psych | Feeling of Failure | Sym: Psych: Feeling of Failure: |
| Sym | Psych | Psychomotor Agitation or Retardation | Sym: Psych: Psychomotor Agitation or Retardation: |
| Sym | Psych | Sadness | Sym: Psych: Sadness: |
| Sym | Psych | Anhedonia | Sym: Psych: Anhedonia: |
| Sym | Psych | Manic Episodes | Sym: Psych: Manic Episodes: |
| Sym | Psych | Change in Personality | Sym: Psych: Change in Personality: |
| Sym | Psych | Paranoia | Sym: Psych: Paranoia: |
| Sym | Psych | Hallucinations | Sym: Psych: Hallucinations: |
| Sym | Psych | Irritability/Mood Swings | Sym: Psych: Irritability/Mood Swings: |
| Sym | Psych | Wake up Unrefreshed | Sym: Psych: Wake up Unrefreshed: |
| Sym | Psych | Stress | Sym: Psych: Stress: |
| Sym | Psych | Suicidality | Sym: Psych: Suicidality: |
| Sym | Psych | Homicidality | Sym: Psych: Homicidality: |
| Sym | Psych | Changes in Sexual Arousal | Sym: Psych: Changes in Sexual Arousal: |
| Sym | Endo | | Sym: Endo:: |
| Sym | Endo | Heat Intolerance | Sym: Endo: Heat Intolerance: |
| Sym | Endo | Cold Intolerance | Sym: Endo: Cold Intolerance: |
| Sym | Endo | Excessive Thirst (Polydipsia) | Sym: Endo: Excessive Thirst (Polydipsia): |

TABLE 1-continued

| Entity 1 | Entity 2 | Entity 3 | Combined Label that will show up in labeling tool |
|---|---|---|---|
| Sym | Endo | Excessive Appetite (Polyphagia) | Sym: Endo: Excessive Appetite (Polyphagia): |
| Sym | Endo | Excessive Sweating | Sym: Endo: Excessive Sweating: |
| Sym | Endo | Flushing | Sym: Endo: Flushing: |
| Sym | Endo | Hot Flashes (Vasomotor symptoms) | Sym: Endo: Hot Flashes (Vasomotor symptoms): |
| Sym | Heme/Lymph | | Sym: Heme/Lymph:: |
| Sym | Heme/Lymph | Lymph Node Enlargement/Tenderness | Sym: Heme/Lymph: Lymph Node Enlargement/Tenderness: |
| Sym | Heme/Lymph | Easy Bruising | Sym: Heme/Lymph: Easy Bruising: |
| Sym | Heme/Lymph | Easy Bleeding | Sym: Heme/Lymph: Easy Bleeding: |
| Sym | Immuno | | Sym: Immuno:: |
| Sym | Immuno | Anaphylaxis | Sym: Immuno: Anaphylaxis: |
| Sym | Immuno | Hives (Urticaria) | Sym: Immuno: Hives (Urticaria): |
| Sym | Immuno | Frequent Sneezing | Sym: Immuno: Frequent Sneezing: |
| Sym | Immuno | Seasonal Allergies | Sym: Immuno: Seasonal Allergies: |
| Sym | Immuno | Environmental Allergies | Sym: Immuno: Environmental Allergies: |
| Sym | Immuno | Exposure to infectious diseases (TB, HIV, etc.) | Sym: Immuno: Exposure to infectious diseases (TB, HIV, etc.): |
| Sym | | | Sym::: |
| Sym | Suggest Entity | | Sym: Suggest Entity:: |

What is claimed is:

1. A method of facilitating annotation of a recording of a medical practitioner-patient conversation, comprising the steps of:
generating, by a computing device, a display of a transcript of the recording;
receiving, by the computing device and for each highlighted span of text of one or more highlighted spans of text in the transcript, a user-selection of a label from a list of labels, wherein each label in the list of labels encodes a medical entity and one or more attributes of the medical entity appearing in the given span, wherein medical entities indicate categories of medical topics, and wherein medical attributes indicate descriptive properties or characteristics of an associated medical entity;
responsive to the user selection, associating, by the computing device, the selected label with a respective highlighted span of text;
detecting, by the computing device, a user interaction with the displayed transcript, wherein the user interaction comprises of a user relating two different highlighted spans of text by utilizing an input device of the computing device, and wherein the computing device is configured to interpret the user interaction to be an indication that the two user-related different highlighted spans of text are medically related to a same health condition of the patient;
generating, by the computing device and responsive to the detecting, a grouping of respective labels associated with the two user-related different highlighted spans of text; and
training, based on a training example comprising the highlighted transcript and the grouping of respective labels associated with the two user-related different highlighted spans of text, a machine learning model to automatically annotate an additional transcript of an additional medical practitioner-patient conversation.

2. The method of claim 1, wherein the transcribed recording is indexed to time segment information.

3. The method of claim 1, wherein the highlighting corresponds to words or groups of words to be highlighted, and not individual characters.

4. The method of claim 1, wherein the medical entities are selected from a list of medical entities consisting of medications, procedures, symptoms, vitals, lab results, chief complaint, social history, medical conditions, surgery, imaging, provider, vaccine, reproductive history, examination, and medical equipment.

5. The method of claim 4, wherein at least one of the medical entities is arranged in a hierarchical manner.

6. The method of claim 5, wherein at least one of the medical entities includes a symptom medical entity and different parts of the body within the symptom medical entity.

7. The method of claim 4, wherein one of the medical entities consists of a symptom medical entity and wherein the symptom medical entity includes attributes of at least severity, frequency, onset, or location.

8. The method of claim 1, further comprising supplying the transcript to a pre-labeling system and receiving from the pre-labeling system a pre-annotated transcript containing suggested labels for spans of text in the transcript.

9. The method of claim 8, further comprising displaying a suggested label from the pre-annotated transcript and providing a tool to either reject or accept the suggested label.

10. The method of claim 8, wherein the pre-labeling system includes a named entity recognition model trained on at least one of medical textbooks, a lexicon of clinical terms, clinical documentation in electronic health records, and annotated transcripts of doctor-patient conversations.

11. The method of claim 1, wherein the user selection comprises a key stroke, a mouse action, or a combination of both.

12. The method of claim 1, providing a scrollable list of available labels and a search box for entering a search term for searching through the list of available labels, and wherein the user selection comprises a key stroke, a mouse action, or a combination of both, to assign a label.

13. A system for facilitating annotation of a recording of a medical practitioner-patient conversation, comprising:
a computing device; and
data storage, wherein the data storage has stored thereon computer-executable instructions that, when executed by the one or more processors, cause the computing device to carry out functions comprising:
displaying a transcript of the recording;
receiving, by the computing device and for each highlighted span of text of one or more highlighted spans of text in the transcript, a a user selection of a label from a list of labels, wherein each label in the list of labels encodes a medical entity and one or more attributes of the medical entity appearing in the given span, wherein medical entities indicate categories of medical topics, and wherein medical attributes indicate descriptive properties or characteristics of an associated medical entity;
responsive to the user selection, associating, by the computing device, the selected label with a respective highlighted span of text;
detecting, by the computing device, a user interaction with the displayed transcript, wherein the user interaction comprises of a user relating two different highlighted spans of text by utilizing an input device of the computing device, and wherein the computing device is configured to interpret the user interaction to be an indication that the two user-related different highlighted spans of text are medically related to a same health condition of the patient;
generating, by the computing device and responsive to the detecting, a grouping of respective labels associated with the two user-related different highlighted spans of text; and
training, based on a training example comprising the highlighted transcript and the grouping of respective labels associated with the two user-related different highlighted spans of text, a machine learning model to automatically annotate an additional transcript of an additional medical practitioner-patient conversation.

14. The system of claim 13, wherein the transcribed recording is indexed to time segment information.

15. The system of claim 13, wherein the highlighting corresponds to words or groups of words to be highlighted, and not individual characters.

16. The system of claim 13, wherein the medical entities are selected from a list of medical entities consisting of medications, procedures, symptoms, vitals, lab results, chief complaint, conditions, social history, medical conditions, surgery, imaging, provider, vaccine, reproductive history, examination, and medical equipment.

17. The system of claim 16, wherein at least one of the medical entities is predefined in a hierarchical manner.

18. The system of claim 17, wherein at least one of the medical entities includes a symptom medical entity and different parts of the body within the symptom medical entity.

19. The system of claim 16, wherein one of the medical entities consists of a symptom medical entity and wherein the symptom medical entity includes attributes of at least severity, frequency, or onset.

20. The system of claim 13, further comprising a pre-labeling system generating a pre-annotated transcript containing suggested labels for spans of text in the transcript.

21. The system of claim 20, wherein the computer-executable instructions comprise instructions that cause the computing device to:
display a suggested label from the pre-annotated transcript, and
wherein the user selection comprises a selection to either reject or accept the suggested label.

22. The system of claim 20, wherein the pre-labeling system includes a named entity recognition model trained on at least one of medical textbooks, a lexicon of clinical terms, clinical documentation in electronic health records, and annotated transcripts of doctor-patient conversations.

23. The system of claim 13, further comprising a system for generating a machine learning model configured to automatically generate annotated transcribed audio recordings.

24. The system of claim 13, further comprising a system for generating a machine learning model configured to generate health predictions.

25. The system of claim 13, wherein the user selection comprises a key stroke, a mouse action, or a combination of both.

26. The system of claim 13, providing a scrollable list of available labels and a search box for entering a search term for searching through the list of available labels, and wherein the user selection comprises a key stroke, a mouse action, or a combination of both, to assign a label.

27. A method of facilitating annotation of a recording of a conversation, comprising the steps of:
a) generating, by an interactive graphical user interface, a display of a transcript of the recording;
b) providing, by the interactive graphical user interface, a highlighting tool for highlighting one or more spans of text in the transcript consisting of one or more words;
c) providing, by the interactive graphical user interface, a label selection tool for assigning a one or more labels from a list of labels to the one or more highlighted spans of text, wherein the label selection tool includes a feature for searching through predefined labels available for assignment to the one or more highlighted span of text, and wherein the labels encode entities and attributes of the entities, wherein the entities indicate categories of topics related to the recording, and wherein the attributes indicate descriptive properties or characteristics of an associated entity;
d) providing, by the interactive graphical user interface, a selection tool for indicating related highlighted spans of texts;
e) detecting, by the interactive graphical user interface, a user interaction with the transcript, wherein the user interaction comprises of a user relating two different highlighted spans of text by utilizing the selection tool, and wherein the user interaction is an indication that the two user-related different highlighted spans of text are related to a same concept;
f) generating, responsive to the detecting, a grouping of the respective labels associated with the two user-related different highlighted spans of text; and
g) training, based on a training example comprising the highlighted transcript and the grouping of respective labels associated with the two user-related different highlighted spans of text, a machine learning model to automatically annotate an additional transcript of an additional conversation.

28. The method of claim 27, wherein the recording consists of a recording between a patient and medical professional.

29. The method of claim 27, further comprising supplying the transcript to a pre-labeling system and receiving from the pre-labeling system a pre-annotated transcript containing suggested labels for spans of text in the transcript.

30. The method of claim 27, wherein the transcribed recording is indexed to time segment information.

31. The method of claim 27, wherein the tool b) and the tool d) comprise key stroke(s), mouse action or a combination of both.

32. The method of claim 27, wherein the feature for searching in tool c) comprises a display of a scrollable list of available labels and a search box for entering a search term for searching through the list of available labels, and wherein tool c) further comprises key stroke(s), mouse action or a combination of both to assign a label.

33. The method of claim 29, wherein the tool c) further comprises a display of a suggested label from the pre-annotated transcript and tools to either reject or accept the suggested label.

34. The method of claim 27, wherein at least one of the entities is defined in a hierarchical manner.

35. The method of claim 1, wherein the user interaction with the displayed transcript comprises a keyboard action, a mouse action, or a combination of both.

36. The method of claim 1, further comprising:
displaying, by the computing device and responsive to the detecting, the two different highlighted spans of text indicated as medically related to the same health condition of the patient and a respective position identifier indicating a position of each highlighted span of text in the transcript.

37. The method of claim 1, further comprising:
displaying, by the computing device and responsive to the detecting, the respective labels corresponding to the two different highlighted spans of texts indicated as medically related to the same health condition of the patient and a respective position identifier indicating a position of each highlighted span of text in the transcript.

38. The method of claim 1, further comprising:
displaying, alongside the display of the transcript, a list comprising (i) each highlighted span of text in the grouping, (ii) a respective position identifier indicating a position of the highlighted span in the transcript, and (iii) a respective set of labels corresponding to the highlighted span of text, wherein the displaying of the list occurs contemporaneously with the receiving of the user generated grouping.

\* \* \* \* \*